(12) United States Patent
Ni et al.

(10) Patent No.: US 7,494,669 B2
(45) Date of Patent: Feb. 24, 2009

(54) DELIVERY OF PHYSIOLOGICAL AGENTS WITH IN-SITU GELS COMPRISING ANIONIC POLYSACCHARIDES

(75) Inventors: Yawei Ni, College Station, TX (US); Kenneth M. Yates, Keller, TX (US)

(73) Assignee: Carrington Laboratories, Inc., Irving, TX (US)

( * ) Notice: Subject to any disclaimer, the term of this patent is extended or adjusted under 35 U.S.C. 154(b) by 138 days.

(21) Appl. No.: 10/652,622

(22) Filed: Aug. 29, 2003

(65) Prior Publication Data

US 2005/0084534 A1   Apr. 21, 2005

Related U.S. Application Data

(63) Continuation-in-part of application No. 09/795,897, filed on Feb. 28, 2001, now Pat. No. 6,777,000.

(51) Int. Cl.
*A61K 9/14* (2006.01)
*A61K 39/00* (2006.01)
*A01N 61/00* (2006.01)

(52) U.S. Cl. ........................ 424/488; 424/184.1; 514/1; 514/2; 530/300; 530/350

(58) Field of Classification Search ........................ None
See application file for complete search history.

(56) References Cited

U.S. PATENT DOCUMENTS

| | | | |
|---|---|---|---|
| 2,629,665 A * | 2/1953 | Gordon | ........................ 426/548 |
| 3,622,559 A | 11/1971 | Wiles et al. | |
| 3,946,110 A * | 3/1976 | Hill | ........................ 514/161 |
| 3,982,003 A | 9/1976 | Mitchell et al. | |
| 4,016,351 A | 4/1977 | Eschinasi | |
| 4,199,560 A | 4/1980 | Gyarmati et al. | |
| 4,305,933 A | 12/1981 | Wiczer | |
| 4,497,838 A | 2/1985 | Bonnell | |
| 4,500,510 A | 2/1985 | Goldstein | |
| 4,613,500 A | 9/1986 | Suzuki et al. | |
| 4,652,441 A | 3/1987 | Okada et al. | |
| 4,711,782 A | 12/1987 | Okada et al. | |
| 4,725,438 A | 2/1988 | Leazer | |
| 4,735,935 A | 4/1988 | McAnalley et al. | |
| 4,842,866 A | 6/1989 | Horder et al. | |
| 4,847,091 A | 7/1989 | Illum | |
| 4,851,224 A | 7/1989 | McAnalley et al. | |
| 4,891,226 A | 1/1990 | Bremecker et al. | |
| 4,917,890 A | 4/1990 | McAnalley | |
| 4,917,893 A | 4/1990 | Okada et al. | |
| 4,925,677 A | 5/1990 | Feijen | |
| 4,957,907 A | 9/1990 | McAnalley et al. | |
| 4,959,214 A | 9/1990 | McAnalley et al. | |
| 4,966,892 A | 10/1990 | McAnalley et al. | |
| 4,978,528 A * | 12/1990 | Degre | ........................ 424/94.4 |
| 4,981,875 A | 1/1991 | Leusner et al. | |
| 5,059,189 A | 10/1991 | Cilento et al. | |
| 5,061,492 A | 10/1991 | Okada et al. | |
| 5,064,650 A | 11/1991 | Lew | |
| 5,071,644 A | 12/1991 | Viegas et al. | |
| 5,079,018 A | 1/1992 | Ecanow | |
| 5,106,616 A | 4/1992 | McAnalley et al. | |
| 5,118,673 A | 6/1992 | Carpenter et al. | |
| 5,122,597 A | 6/1992 | Barritault et al. | |
| 5,130,418 A | 7/1992 | Thompson | |
| 5,147,648 A | 9/1992 | Bannert | |
| 5,188,825 A | 2/1993 | Iles et al. | |
| 5,191,067 A | 3/1993 | Lappi et al. | |
| 5,192,802 A | 3/1993 | Rencher | |
| 5,204,108 A | 4/1993 | Illum | |
| 5,208,031 A | 5/1993 | Kelly | |
| 5,217,954 A | 6/1993 | Foster et al. | |
| 5,238,917 A | 8/1993 | Fujii et al. | |
| 5,266,318 A | 11/1993 | Taylor-McCord | |
| 5,284,659 A | 2/1994 | Cherukuri et al. | |
| 5,288,498 A | 2/1994 | Stanley et al. | |
| 5,288,500 A | 2/1994 | Ibsen | |
| 5,308,838 A | 5/1994 | McAnalley et al. | |
| 5,310,883 A | 5/1994 | Seddon et al. | |
| 5,314,915 A | 5/1994 | Rencher | |
| 5,318,780 A | 6/1994 | Viegas et al. | |
| 5,356,630 A | 10/1994 | Laurencin et al. | |

(Continued)

FOREIGN PATENT DOCUMENTS

EP    0 306 454    3/1989

(Continued)

OTHER PUBLICATIONS

Albersheim et al., "Splitting of Pectin Chain Molecules in Neutral Solutions," *Biochemistry and Biophysics*, 90:46-51 (1960).

(Continued)

*Primary Examiner*—Richard Schnizer
(74) *Attorney, Agent, or Firm*—Ballard Spahr Andrews & Ingersoll, LLP

(57) ABSTRACT

In-situ gelation of a pectic substance. Composition, method of preparation, and method of use of a pectin in-situ gelling formulation for the delivery and sustained release of a physiologically active agent to the body of an animal. The pectin can be isolated from *Aloe vera*.

78 Claims, 11 Drawing Sheets

U.S. PATENT DOCUMENTS

| | | | |
|---|---|---|---|
| 5,362,424 A | 11/1994 | Lee et al. | |
| 5,387,415 A | 2/1995 | Wunderlich et al. | |
| 5,409,703 A | 4/1995 | McAnalley et al. | |
| 5,422,340 A | 6/1995 | Ammann et al. | |
| 5,435,997 A | 7/1995 | Burns | |
| 5,436,225 A * | 7/1995 | Hirabayashi et al. | 504/289 |
| 5,441,943 A | 8/1995 | McAnalley et al. | |
| 5,443,830 A | 8/1995 | McAnalley et al. | |
| 5,453,492 A | 9/1995 | Butzow et al. | |
| 5,464,815 A | 11/1995 | Chamow et al. | |
| 5,503,822 A | 4/1996 | Schulman | |
| 5,505,966 A | 4/1996 | Edman et al. | |
| 5,508,043 A | 4/1996 | Krishnamurthy | |
| 5,512,306 A | 4/1996 | Carlsson et al. | |
| 5,514,652 A | 5/1996 | Watanuki et al. | |
| 5,525,634 A | 6/1996 | Sintov et al. | |
| 5,545,673 A | 8/1996 | Kelly | |
| 5,552,528 A | 9/1996 | Burgess et al. | |
| 5,571,531 A | 11/1996 | McDermott et al. | |
| 5,576,288 A | 11/1996 | Lappi et al. | |
| 5,578,307 A | 11/1996 | Wunderlich et al. | |
| 5,578,335 A | 11/1996 | Grassin et al. | |
| 5,587,175 A | 12/1996 | Viegas et al. | |
| 5,589,451 A | 12/1996 | Wilson | |
| 5,599,551 A | 2/1997 | Kelly | |
| 5,604,204 A | 2/1997 | Ammann et al. | |
| 5,612,053 A * | 3/1997 | Baichwal et al. | 424/440 |
| 5,612,211 A | 3/1997 | Wilson et al. | |
| 5,614,496 A | 3/1997 | Dunstan et al. | |
| 5,622,717 A | 4/1997 | Fuisz | |
| 5,639,795 A | 6/1997 | Friedman et al. | |
| 5,645,827 A | 7/1997 | Marlin et al. | |
| 5,648,399 A | 7/1997 | Friedman et al. | |
| 5,651,987 A | 7/1997 | Fuisz | |
| 5,656,587 A | 8/1997 | Sporn et al. | |
| 5,656,598 A | 8/1997 | Dunstan et al. | |
| 5,656,734 A | 8/1997 | Ehrlich et al. | |
| 5,665,870 A | 9/1997 | Rubin et al. | |
| 5,674,495 A | 10/1997 | Bowersock et al. | |
| 5,690,954 A | 11/1997 | Illum | |
| 5,693,775 A | 12/1997 | Nathans et al. | |
| 5,703,047 A | 12/1997 | Wilson | |
| 5,707,644 A | 1/1998 | Illum | |
| 5,714,458 A | 2/1998 | Adami et al. | |
| 5,738,865 A | 4/1998 | Baichwal et al. | |
| 5,753,622 A | 5/1998 | Buret et al. | |
| 5,760,102 A | 6/1998 | Hall et al. | |
| 5,770,582 A | 6/1998 | von Borstel et al. | |
| 5,804,212 A | 9/1998 | Illum | |
| 5,811,123 A | 9/1998 | Fuisz | |
| 5,840,332 A | 11/1998 | Lerner et al. | |
| 5,849,327 A | 12/1998 | Berliner et al. | |
| 5,863,554 A | 1/1999 | Illum | |
| 5,866,619 A | 2/1999 | Sintov et al. | |
| 5,900,238 A | 5/1999 | Gombotz et al. | |
| 5,902,796 A | 5/1999 | Shand et al. | |
| 5,929,051 A * | 7/1999 | Ni et al. | 514/54 |
| 5,935,604 A | 8/1999 | Illum | |
| 5,942,242 A * | 8/1999 | Mizushima et al. | 424/434 |
| 5,948,749 A | 9/1999 | Igarashi et al. | |
| 5,958,443 A | 9/1999 | Viegas et al. | |
| 6,033,651 A | 3/2000 | Dolak et al. | |
| 6,060,078 A | 5/2000 | Lee | |
| 6,063,915 A | 5/2000 | Hansen et al. | |
| 6,083,531 A | 7/2000 | Humbert-Droz et al. | |
| 6,083,540 A | 7/2000 | Christensen et al. | |
| 6,103,269 A | 8/2000 | Wunderlich et al. | |
| 6,133,440 A | 10/2000 | Qiu et al. | |
| 6,136,334 A | 10/2000 | Viegas et al. | |
| 6,139,880 A | 10/2000 | Dolak et al. | |
| 6,149,940 A | 11/2000 | Maggi et al. | |
| 6,159,491 A | 12/2000 | Durrani | |
| 6,171,594 B1 | 1/2001 | Nielsen | |
| 6,174,549 B1 | 1/2001 | Greenshields et al. | |
| 6,197,327 B1 | 3/2001 | Harrison et al. | |
| 6,197,346 B1 | 3/2001 | Mathiowitz et al. | |
| 6,210,710 B1 | 4/2001 | Skinner | |
| 6,217,908 B1 | 4/2001 | Mathiowitz et al. | |
| 6,228,387 B1 | 5/2001 | Borod | |
| 6,228,396 B1 | 5/2001 | Watts | |
| 6,231,888 B1 | 5/2001 | Lerner et al. | |
| 6,248,360 B1 | 6/2001 | Choi et al. | |
| 6,261,574 B1 | 7/2001 | Costello | |
| 6,274,548 B1 | 8/2001 | Ni et al. | |
| 6,284,273 B1 | 9/2001 | Lenaerts et al. | |
| 6,290,964 B1 | 9/2001 | Shupe et al. | |
| 6,309,675 B1 | 10/2001 | Sobczak | |
| 6,310,089 B1 * | 10/2001 | Watts et al. | 514/444 |
| 6,313,103 B1 | 11/2001 | Ni et al. | |
| 6,333,194 B1 | 12/2001 | Levy et al. | |
| 6,342,251 B1 | 1/2002 | Illum et al. | |
| 6,350,469 B1 | 2/2002 | Daggy et al. | |
| 6,355,276 B1 | 3/2002 | Illum et al. | |
| 6,358,525 B1 | 3/2002 | Guo et al. | |
| 6,365,200 B1 | 4/2002 | Birnholz et al. | |
| 6,365,624 B1 | 4/2002 | Davidson et al. | |
| 6,368,639 B1 | 4/2002 | Farooqui et al. | |
| 6,375,963 B1 | 4/2002 | Repka et al. | |
| 6,375,988 B1 | 4/2002 | Suzuki et al. | |
| 6,383,495 B1 | 5/2002 | Ramakrishna et al. | |
| 6,383,513 B1 | 5/2002 | Watts et al. | |
| 6,387,394 B1 | 5/2002 | Baichwal et al. | |
| 6,387,408 B1 | 5/2002 | Illum et al. | |
| 6,387,917 B1 | 5/2002 | Illum et al. | |
| 6,391,318 B1 | 5/2002 | Illum et al. | |
| 6,413,494 B1 | 7/2002 | Lee et al. | |
| 6,413,941 B1 | 7/2002 | Garnett et al. | |
| 6,416,779 B1 | 7/2002 | D'Augustine et al. | |
| 6,423,345 B2 | 7/2002 | Bernstein et al. | |
| 6,432,440 B1 | 8/2002 | Watts et al. | |
| 6,436,461 B1 | 8/2002 | Bouwmeesters et al. | |
| 6,451,351 B1 | 9/2002 | Kawashima et al. | |
| 6,455,066 B1 | 9/2002 | Fischer et al. | |
| 6,465,626 B1 | 10/2002 | Watts et al. | |
| 6,475,526 B1 | 11/2002 | Smith | |
| 6,517,868 B2 | 2/2003 | Fassihi et al. | |
| 6,518,239 B1 * | 2/2003 | Kuo et al. | 514/2 |
| 6,531,152 B1 | 3/2003 | Lerner et al. | |
| 6,534,065 B1 | 3/2003 | Makin et al. | |
| 6,541,035 B1 | 4/2003 | Pallado et al. | |
| 6,551,631 B2 | 4/2003 | Shupe et al. | |
| 6,552,024 B1 | 4/2003 | Chen et al. | |
| 6,558,792 B1 | 5/2003 | Vaabengaard et al. | |
| 6,562,363 B1 | 5/2003 | Mantelle et al. | |
| 6,569,463 B2 | 5/2003 | Patel et al. | |
| 6,582,728 B1 | 6/2003 | Platz et al. | |
| 6,596,297 B2 | 7/2003 | Neurath et al. | |
| 6,632,457 B1 | 10/2003 | Sawhney | |
| 6,824,790 B2 | 11/2004 | Yatvin | |
| 7,022,683 B1 | 4/2006 | Ni et al. | |
| 2001/0043949 A1 | 11/2001 | Delgado | |
| 2001/0046518 A1 | 11/2001 | Sawhney | |
| 2001/0046519 A1 | 11/2001 | Illum et al. | |
| 2001/0051613 A1 | 12/2001 | Illum et al. | |
| 2001/0053359 A1 | 12/2001 | Watts et al. | |
| 2001/0055569 A1 | 12/2001 | Davis et al. | |
| 2002/0001610 A1 | 1/2002 | Cohen et al. | |
| 2002/0001619 A1 | 1/2002 | Goldenberg et al. | |
| 2002/0009418 A1 | 1/2002 | Steiner et al. | |
| 2002/0009438 A1 | 1/2002 | Shupe et al. | |
| 2002/0044972 A1 | 4/2002 | Davis et al. | |
| 2002/0058624 A1 | 5/2002 | Hanyu et al. | |
| 2002/0068091 A1 | 6/2002 | Davis et al. | |
| 2002/0086829 A1 | 7/2002 | Gefter | |

| | | | |
|---|---|---|---|
| 2002/0098198 | A1 | 7/2002 | Watts et al. |
| 2002/0176846 | A1 | 11/2002 | Hastedt et al. |
| 2002/0197324 | A1 | 12/2002 | Watts et al. |
| 2003/0039665 | A1 | 2/2003 | Illum et al. |
| 2003/0059440 | A1 | 3/2003 | Clarot et al. |
| 2003/0060486 | A1 | 3/2003 | Jacob et al. |
| 2003/0068376 | A1 | 4/2003 | Chen et al. |
| 2003/0068378 | A1 | 4/2003 | Chen et al. |
| 2003/0077296 | A1 | 4/2003 | Denton et al. |
| 2003/0118653 | A1 | 6/2003 | Chen et al. |
| 2003/0138505 | A1 | 7/2003 | Fischer et al. |
| 2003/0143274 | A1 | 7/2003 | Viegas et al. |
| 2003/0152629 | A1 | 8/2003 | Shefer et al. |

FOREIGN PATENT DOCUMENTS

| | | |
|---|---|---|
| EP | 1 110 550 | 6/2001 |
| JP | 62255415 | 11/1987 |
| JP | 06205687 | 7/1994 |
| SU | 324263 | 12/1971 |
| WO | WO 98/47535 | 10/1998 |
| WO | WO 99/27905 | 6/1999 |

OTHER PUBLICATIONS

Anderson, "Human Gene Therapy," *Nature*, 392:25-30 (1998).
Anderson et al., "Protection of Cattle Against Rinderpest by Intranasal Immunisation with a Dry Powder Tissue Culture Vaccine," *Vaccine*, 19:840-843 (2001).
Ashford et al., "Studies on Pectin Formulations for Colonic Drug Delivery," *Journal of Controlled Release*, 30:225-232 (1994).
Ashford et al., "An Evaluation of Pectin as a Carrier for Drug Targeting to the Colon," *Journal of Controlled Release*, 26:213-220 (1993).
Austin et al., "The Effect of Calcium Pectinate Gel Implants on the Healing of Experimental Defects in the Femora of Albino Rats," *S. Afr. J. Med. Sci.*, 38:55-60 (1973).
Axelos et al., "Influence of the Substitutents of the Carboxyl Groups and of the Rhamnose Content of the Solution Properties and Flexibility of Pectins," *Int. J. Biol. Macromol.*, 13:77-82 (1991).
Aydin et al., "Preparation and Evaluation of Pectin Beads," *Int'l Journal of Pharmaceutics*, 137:133-136 (1996).
Blumenkrantz et al., "New Method for Quantitative Determination of Uronic Acids," *Analytical Biochenistry*, 54:484-489 (1973).
Cohen et al., "A Novel In Situ-Forming Ophthalmic Drug Delivery System from Alginates Undergoing Gelation in the Eye," *Journal of Controlled Release*, 44:201-208 (1997).
Davis et al., "Absorption Enhancers for Nasal Drug Delivery," *Clinical Pharmacokinetics*, 42(13):1107-1128 (2003).
Davis, "Nasal Vaccines," *Advanced Drug Delivery Reviews*, 51:21-42 (2001).
Dyer et al., "Nasal Delivery of Insulin Using Novel Chitosan Based Formulations: A Comparative Study in Two Animal Models Between Simple Chitosan Formulations and Chitosan Nanoparticles," *Pharmaceutical Research*, 19(7):998-1008 (2002).
Eck et al., "Gene-Based Therapy," *Goodman and Gilman's Pharmacacological Basis of Therapeutics*, McGraw-Hill Publishers, 5:77-101 (1995).
England et al., "Nasal pH Measurement: A Reliable and Repeatable Parameter," *Clinical Otolarygology*, 24:67-68 (1999).
Fisher et al., "Assessment of Accidental Intakes of Uranyl Acetylacetonate (UAA)," *Radiation Protection Dosimetry*, 53(1-4):263-267 (1994).
Fishman et al., "Characterization of Pectin, Flash-Extracted from Orange Albedo by Microwave Heating, Under Pressure," *Carbohydrate Research*, 323:126-138 (2000).
Garnier et al., "Selectivity and Cooperativity in the Binding of Calcium Ions by Pectins," *Carbohydrate Research*, 256:71-81 (1994).
Garnier et al., "Phase Diagrams of Pectin—Calcium Systems: Influence of pH, Ionic Strength, and Temperature on the Gelation of Pectins with Different Degrees of Methylation," *Carbohydrate Research*, 240:219-232 (1993).

Gemeiner et al., "Calcium Pectate Gel could be a Better Alternative to Calcium Alginate Gel in Multiple Applications of Immobilized Cells," *Progress in Biotechnology*, 2:76-83 (1996).
Gurny et al., "Ocular Theraphy with Nanoparticulate Systems for Controlled Drug Delivery," *Journal of Controlled Release*, 2:353-361 (1985).
Illum, "Nasal Drug Delivery: New Developments and Strategies," *Drug Discovery Today*, 7(23):1184-1189 (2002).
Ireson et al., "Comparison of nasal pH values in Black and White Individuals with Normal and High Blood Pressure," *Clinical Science*, 100:327-333 (2001).
Ishikawa et al., "Insoluble Powder Formulation as an Effective Nasal Drug Delivery System," *Pharmaceutical Research*, 19(8):1097-1104 (2002).
Jarvis et al., "Structure and Properties of Pectin Gels in Plant Cell Walls," *Plant, Cell and Environment*, 7:153-164 (1984).
Jeong et al., "Biodegradable Block Copolymers as Injectable Drug-Delivery Systems," *Nature*, 388:860-862 (1997).
Jeong et al., "Drug Release from Biodegradable Injectable Thermosensitive Hydrogel of PEG-PLGA-PEG Triblock Copolymers," *Journal of Controlled Release*, 63:155-163 (2000).
Jones et al., "A Nasal Proteosome™ Influenza Vaccine Containing Baculovirus-Derived Hemagglutinin Induces Protective Mucosal and Systemic Immunity," *Vaccine*, 21:3706-3712 (2003.
Kajiwara et al., "Gels Handbook," *Academic Press*, vol. 1, Chapter 1, Sections 1-2, pp. 3-25 (2001, 1997).
Langer, "Drug Delivery and Targeting," *Nature*, 392(Supp.):5-10 (1998).
Licalsi et al., "A Power Formulation of Measles Vaccine for Aerosol Delivery," *Vaccine*, 19:2629-2636 (2001).
Lin et al., "Carbopol/Pluronic Phase Change Solutions for Ophthalmic Drug Delivery," *Journal of Controlled Release*, 69:379-388 (2000).
Lorin et al., "Quantitative Composition of Nasal Secretions in Normal Subjects," *Journal of Laboratory and Clinical Medicine*, 80(2):275-281 (1972).
Malcolmson et al., "Dry Powder Formulations for Pulmonary Delivery," *PSTT*, 1(9):394-398 (1998).
Mandal et al., "Structure of the $_D$-Galactan Isolated From Aloe barbadensis Miller," *Carbohydrate Research*, 86:247-257 (1980).
Mandal et al., "Characterisation of Polysaccharides of Aloe Barbadensis Miller: Part III—Structure of an Acidic Oligosaccharide," *Indian Journal of Chemistry*, 22(b):890-893 (1983).
Maness et al., "Determination of the Degree of Methyl Esterification of Pectins in Small Samples by Selective Reduction of Esterified Galacturonic Acid to Galactose," *Analytical Biochemistry*, 183:346-352 (1990).
Mitterhauszerova et al., "Interaction of Aminopyrine, 4-Aminoantipyrine, Nicotine Amide, and P-Aminosalicylate with Pectic Acid," *Pharmacology*, L11:501-507 (1983).
Miyazaki et al., "Oral Mucosal Bioadhesive Tablets of Pectin and HPMC: In Vitro and In Vivo Evaluation," *Int'l Journal of Pharmaceutics*, 204:127-132 (2000).
Moe et al., "Alginates," *Food Polysaccharides and Their Applications*, 9:245-286 (1995).
Munjeri et al., "Hydrogel Beads Based on Amidated Pectins for Colon-Specific Drug Delivery: The Role of Chitosan in Modifying Drug Release," *Journal of Controlled Release*, 46:273-278 (1997).
Nolan et al., "Safety and Immunogenicity of a Live-Attenuated Influenza Vaccine Blended and Filled at Two Manufacturing Facilities," *Vaccine*, 21:1224-1231 (2003).
Nurmukhambetova et al., "Interaction of Cephedrin with Polyelectrolytes," *News of the Nat'l Academy of Sciences of Republic of Kazakhstan, Chemical Series*, 3:58-61 (1995) (English translation provided).
Piculell, "Gelling Carrageenans," *Food Polysaccharides and Their Applications*, 8:205-239 (1995).
Pilnik et al., "Gelling Agents (Pectins) From Plants For The Food Industry" *Advances in Plant Cell Biochemistry and Biotechnology*, 1:219-270 (1992).
Plante et al., "Nasal Immunization with Subunit Proteosome Influenza Vaccines Induces Serum HAI, Musosal IgA and Protection Against Influenza Challenge," *Vaccine*, 20:218-225 (2002).

Putney et al., "Improving Protein Therapeutics with Sustained-Release Formulations," *Nature Biotechnology*, 16:153-157 (1998).

Renard et al., "Pectins in Mild Alkaline Conditions: β-elimination and Kinetics of Dementhylation," *Progress in Biotechnology, Pectins and Pectinases*, 14:603-608 (1996).

Richardson et al., "Novel Vaginal Delivery Systems for Calcitonin: I. Evaluation of HYAFF/Calcitonin Microspheres in Rats," *Int'l Journal of Pharmaceutics*, 115:9-15 (1995).

Rolin, "Pectin," in Industrial Gums, Academic Press, New York, Chapter 10, p. 258-293 (1993).

Romano et al., "Latest Developments in Gene Transfer Technology: Achievements, Perspectives, and Controversies over Therapeutic Applications," *Stem Cells*, 18:19-39 (2000).

Rozier et al., "Gelrite®: A Novel, Ion-Activated, In-Situ Gelling Polymer for Ophthalmic Vehicles. Effect on Bioavailability of Timolol," *Int'l Journal of Pharmaceutics*, 57:163-168 (1989).

Rydén et al., "Effect of Polymers and Microspheres on the Nasal Absorption of Insulin in Rats," *Int'l J. Pharm.*, 83:1-10 (1992).

Sacchetti et al., "Caffeine Microparticles for Nasal Administration Obtained by Spray Drying," *Int'l Journal of Pharmaceutics*, 242:335-339 (2002).

Schipper et al., "Nasal Insulin Delivery with Dimethyl-β-Cyclodextrin as an Absorption Enhancer in Rabbits: Powder More Effective than Liquid Formulations," *Pharm. Res.*, 10(5):682-686 (1993).

Schols et al., "Complex Pectins: Structure Elucidation Using Enzymes," *In Process in Biotechnology 14. Pectins and Pectinases*, J. Visser and A.G.J. Voragen (Eds.), 3-20 (1996).

Shipunova et al., "Immobilization of Isoniazid on Pectin Compounds," *Institute of Chemical Sciences of Nat'l Academy of Sciences of Republic of Kazakhstan, Alma-ata*, 2:83-88 (1990) (English translation provided).

Singh et al., "A Novel Bioadhesive Intranasal Delivery System for Inactivated Influenza Vaccines," *Journal of Controlled Release*, 70:267-276 (2001).

Somia et al., "Gene Therapy: Trials and Tribulations," *Nature Reviews*, I:91-99 (2000).

Sriamornsak et al., "Calcium Pectinate Gel Beads for Controlled Release Drug Delivery: I. Preparation and In Vitro Release Studies," *Int'l Journal of Pharmaceutics*, 160:207-212 (1998).

Sriamornsak et al., "Calcium pectinate gel beads for controlled release drug delivery: II. Effect of formulation and processing variables on drug release," *J. Microencapsulation*, 16(3):303-313 (1999).

Sriamornsak, "Preliminary Investigation of Some Polysaccharides as a Carrier for Cell Entrapment," *European Journal of Pharmaceutics and Biopharmaceutics*, 46:233-236 (1998).

Sriamornsak et al., "Development of sustained release theophylline pellets coated with calcium pectinate," *J. of Controlled Release*, 47:221-232 (1997).

Stjernschantz et al., "Anatomy and Physiology of the Eye, Physiological Aspects of Ocular Drug Therapy," *Biopharmaceutical Aspects of Ocular Drug Delivery*, 1:1-15 (1993).

Thakur et al., "Chemistry and Uses of Pectin—A Review," *Critical Reviews in Food Science and Nutrition*, 37(1):47-73 (1997).

Tibbits et al., "Calcium Binding and Swelling Behaviour of a High Methoxyl Pectin Gel," *Carbohydrate Research*, 310:101-107 (1998).

Vadnere et al., "Thermodynamic Studies on the Gel-sol Transition of some Pluronic Polyols," *International Journal of Pharmaceutics*, 22:207-218 (1984).

Verma et al., "Gene Therapy—Promises, Problems and Prospects," *Nature*, 389:239-242 (1997).

Voragen et al., "Pectins," *Food Polysaccharides and Their Applications*, 10:287-339 (1995).

Voragen et al., "Determination of the Degree of Methylation and Acetylation of Pectings by H.P.L.C.," *Food Hydrocolloids*, 1:65-70 (1986).

Wakerly et al., "Studies on Amidated Pectins as Potential Carriers in Colonic Drug Delivery," *J. Pharm. Pharmacol.*, 49:622-625 (1997).

Wakerly et al., "Studies on Drug Release from Pectin/Ethycellulose Film-Coated Tablets: A potential Colonic Delivery System," *International Journal of Pharmaceutics*, 153:219-224 (1997).

Yamada, "Contribution of Pectins on Health Care," *Progress in Biotechnology, Pectins and Pectinases*, 14:173-190 (1996).

Zheng et al., "Salt Effects on the Corr-linking Mechanism of Cupric-Induced Sol-Gel Transition in Alginate Solutions," *Carbohydrate Polymers*, 35:215:221 (1998).

Zhubanov et al., "Immobilization of Promedol on Poly-Sugar Supports," *A.B.Bakturov Institute of Chemical Sciences of Nat'l Academy of Sciences of Republic of Kazakhstan, Alma-ata*, (5), 27-31(English translation provided).

Zhubanov et al., "Pectic Acid and Carboxy Methyl Cellulose as Polymer Hosts for Analgesic Promedol," *A.B.Bakturov Institute of Chemical Sciences of Nat'l Academy of Sciences of Republic of Kazakhstan, Alma-ata*, 6:55-58(English translation provided).

Zhubanov et al., "Application of Carboxy Methyl Cellulose and Pectic Acid to Prolong Clophelin Action," *A.B.Bakturov Institute of Chemical Sciences of Nat'l Academy of Sciences of Republic of Kazakhstan, Alma-ata*, 1:61-65 (1993) (English translation provided).

Jordan, "The Jordan Report 20th Anniversary Accelerated Development of Vaccines of 2002," *U.S. Department of Health and Human Services, National Institutes of Health, National Institute of Allergy and Infectious Diseases*, pp. 1-267 (2002).

Aspinall, "Pectins, Plant Gums and Other Plant Polysaccharides," *The Carbohydrates, Chemistry and Biochemistry*, vol. IIB, edited by Pigman and Horton, published by Academic Press, pp. 515-521 (1970).

Bemiller, "An Introduction to Pectins: Structure and Properties," *189th Meeting of the American Chemical Society*, Apr. 28-May 3, 1985, pp. 1-12.

Cardin et al., "Molecular Modeling of Protein-Glyosaminoglycan Interactions," *Arteriosclerosis*, 9(1):21-32 (Jan./Feb. 1989).

Conrad, "Heparin-Binding Proteins—Chapter 1. Heparin vs. Heparin Sulfate," *Academic Press*, pp. 1-5 (1998).

Conrad, "Heparin-Binding Proteins—Chapter 6. Heparinoid/Protein Interactions," *Academic Press*, pp. 183-202 (1998).

Conrad, "Heparin-Binding Proteins—Chapter 9. Fibroblast Growth Factors," *Academic Press*, pp. 301-349 (1998).

Koji et al., "Preparation of pectin gel bead and the drug release profiles," *Kobunshi Gakkai Yokoshu*, 47(12):3510-3511 (1998).

Kravtchenko et al., "Improvement of the Selective Depolymerization of Pectic Substances by Chemical β-Elimination in Aqueous Solution," *Carbohydrate Polymers*, 19:237-242 (1992).

May, "Industrial Pectins: Sources, Production, and Applications," *Carbohydrate Polymers*, 12:79-99 (1990).

Munjeri et al., "In Vivo Behavior of Hydrogel Beads Based on Amidated Pectins," *Drug Delivery*, 5(4):239-241 (1998).

Ovodova et al., "Polysaccharides of Aloe Arboresens," *Plenum Publishing Corporation*, pp. 1-2 (1976).

Radiabi et al., "Structural Studies of the Glucomannan From Aloe Vahombe," *Carbohydrate Research*, pp. 160-170 (1983).

Renard et al., "Structure and Properties of Apple and Sugar-Beet Pectins Extracted by Chelating Agents," *Carbohydrate Research*, 244:99-114 (1993).

Schelessinger et al., "Regulation of Growth Factor Activation by Proteoglycans: What is the Role of the Low Affinity Receptors?" *Cell*, 83:357-360 (Nov. 3, 1995).

Selvendran et al., "Developments in the Isolation and Analysis of Cell Walls From Edible Plants," *Biochemistry of Plant Cell Walls*, pp. 39-79.

Stepanova et al., Fiziol. Aktiv. Veshchestva. Respub. Mezhvedom. Sb., No. 3: 290-301 (1971).

"Polysaccharides in Medicinal Applications," ed. by Severian Dumitriu, publ. by Marcel Dekker, pp. 211-216 (1996).

* cited by examiner

3a

3b a b

DELIVERY OF PHYSIOLOGICAL AGENTS WITH IN-SITU GELS COMPRISING ANIONIC POLYSACCHARIDES

REFERENCE TO RELATED APPLICATIONS

This application is a continuation-in-part of, and claims priority to U.S. Utility application Ser. No. 09/795,987, filed Feb. 28, 2001, now issued as U.S. Pat. No. 6,777,000 the disclosure of which parent application is hereby incorporated herein in its entirety by this reference.

BACKGROUND OF THE INVENTION

A variety of polymer-based drug delivery systems for achieving sustained or controlled drug release have been described (See Langer, Nature, 392 (supplement), 5-10, 1998 and references therein). The goal of many of those systems was typically one or more of prolonging drug release, improving drug bioavailability, and/or providing non-injectable drug delivery systems that improve patient compliance and comfort. The polymers, either synthetic or natural, provide delivery of the various agents by various mechanisms, depending on the properties of the polymer.

The polymer-based systems have been variously formulated as, for example, a liquid, a suspension, an emulsion, a powder comprising microparticle and/or microspheres, a film, or a tablet. The compositions have been administered via various routes or methods, including injection, topical administration, or administration to a mucosal surface of the eye, vaginal, anus, stomach or intestines, oral and nasal cavities, or the lungs. The polymer-based systems have been used to deliver a variety of physiologically active agents, including therapeutics and prophylactic agents, including small molecule- or protein-based drugs, nucleic acids, polysaccharides, fatty acids and esters, cells and fragments thereof, viruses, and vaccines for prevention of infectious diseases.

In-situ gelation has been used in pharmaceutical drug delivery systems and involves gel formation at the site of application to a tissue or body fluid after the composition or formulation has been applied, so as to form a bioadhesive gel to modulate the release of the drug from the gel. In some applications, In-situ gelation permits the drug to be delivered in a liquid form.

Polymers capable of in-situ gelation have been described, including Poloxamer, Pluronics (Vadnere et al., *Int. J. Pharm.*, 22, 207-218, 1984), various copolymers such as PEO-PLLA and PEG-PLGA-PEG (Jeong et al., *Nature* 388, 860-862, 1997; Jeong et al., *J. Controlled Release* 63, 155-163, 2000), cellulose acetophthalate latex (Gurny et al. *J. Controlled Release* 353-361, 1985), Gelrite (Rozier et al., Int. *J. Pham.* 57, 163-168, 1989), Carbopol, and Matrigel. The gel formation is induced by temperature change (Poloxamer, Pluronics, PEO-PLLA diblock copolymer, PEG-PLGA-PEG triblock copolymer, and Matrigel), pH change (cellulose acetophalate latex and Carbopol), or reaction with mono- or di-valent cations (Gelrite and/or alginates). However, most of them require a high polymer concentration for in-situ gel formation (>20%) (Poloxamer, PEO-PLLA diblock copoly, PEG-PLGA-PEG triblock copolymer, cellulose and acetophalate latex). The thermally gelling polymers (Poloxamer, Pluronics, PEO-PLLA diblock copolymer, PEG-PLGA-PEG triblock copolymer, and Matrigel) also have the disadvantage of gelling before administration due to temperature change during packaging or storage. Unfortunately some of these polymers are not biodegradable such as Poloxamer or require manipulation of the temperature before administration (PEO-PLLA diblock copolymer) or during formulation (Pluronics and Gelrite). An ophthalmic in-situ gelling drug delivery formulation consisting of a mixture of Carbopol and Pluronic was found to be more effective than formulations consisting of either one. However, Pluronic is used at 14% (Lin and Sung, *Journal of Controlled Release* 69, 379-388, 2000). Such polymers are therefore not well suited for medical applications in humans and animals. Furthermore, many of these polymers form only a hydrogel which is a viscous but still flowing solution (e.g., Poloxamer and Pluronics).

The in-situ gelation compositions using ionic polysaccharides has been disclosed in U.S. Pat. No. 5,958,443, which discloses compositions comprising a drug, a film forming polymer and a gel forming ionic polysaccharide (such as an alginate). These compositions employed two separately applied components, one being a solution of crosslinking cations, which is applied to the site, and a second liquid component comprising the drug, film forming polymer and an ionic polysaccharide, which is then applied to react with the cross linking ions and form a gel. Various other synthetic and natural polymers have also been used in drug delivery formulations that may or may not have formed crosslinked gels, including starches and modified celluloses, gellan, chitosan, hyaluronic acids, pectins, and the like.

The use of pectins has been mentioned in various drug delivery compositions. Pectins are a biodegradable acidic polysaccharide isolated from plant cell walls. All vegetables and fruits that have been examined appear to contain pectins. Pectins from sugar beets, sunflowers, potatoes, and grapefruits are just a few other well known examples. The chemistry and biology of pectins have been extensively reviewed (Pilnik and Voragen, *Advances in plant biochemistry and biotechnology* 1, 219-270, 1992; Voragen et al, In *Food polysaccharides and their applications*. pp 287-339. Marcel Dekker, Inc. New York, 1995; Schols and Voragen, In *Progress in Biotechnology* 14. *Pectins and pectinases*, J. Visser and A. G. J. Voragen (eds.). pp. 3-20. Elsevier Science Publishers B.V. Amsterdam, 1996).

Pectins have an α-(1→4)-linked polygalacturonic acid (Gal A) polysaccharide polymer backbone intervened by rhamnose residues. The Gal A residues have carboxylic acid substituent groups attached to the saccharide ring, which may be in the form of the carboxylic acid, a salt thereof, or an ester thereof. The Gal A content of most pectins is about 70-75%, and the rhamnose content is typically <2%. The rhamnose residues are α-(1→2)-linked to Gal A residues in the backbone, and induce a T-shaped kink in the backbone chain, leading to more flexibility in the polysaccharide chains. Neutral sugar side chains are attached to the rhamnose residues in the backbone, at the O-3 or O-4 position, and the rhamnose residues tend to be clustered together on the backbone. These rhamnose contain regions comprising the side chains is referred to as a "hairy region" of the pectin, while the long stretches of repeating and unbranched Gal A residues are termed the "smooth region" of the pectin.

The hydroxyl and/or carboxylic acid substituents on the saccharide rings are also often bonded to non-sugar components such as methyl and acetyl groups. The extent of rhamnose insertions and other modifications to the chain and its monomers vary depending on the plant source of the pectin. Methylation occurs at carboxyl groups of the Gal A residues, so as to form carboxylic acid methyl esters. The degree of methylation or methyl-esterification ("DM") if a pectin is defined as the percentage of carboxyl groups (Gal A residues) esterified with methanol. Based on the DM, pectins are divided into two classes, low methoxyl ("LM") pectin with a DM of <50% and a high methoxyl ("HM") pectin with a DM of >50%. Most natural pectins and most commercial pectins, which are typically derived from citrus and apples, are HM pectins.

LM pectins are typically obtained from HM pectins through an artificial chemical or biochemical de-esterification process. Commercial LM pectins typically have a DM of 20-50%. A completely de-esterified pectin is referred as "pectic acid" or "polygalacturonic acid". Pectic acid in the acid form is insoluble but is soluble in the salt form. The common salt form of pectic acid is either sodium or potassium.

Pectins are typically most stable at acidic pH levels between approximately 3-4. Below pH 3, removal of methoxyl and acetyl groups and neutral sugar side chains typically occurs. Under neutral and alkaline conditions, the methyl ester groups of the Gal A residues are known to be saponified to the carboxylic acid or carboxylate form, but the polygalacturonan backbone also breaks through β-elimination-cleavage of glycosidic bonds on the non-reducing ends of methylated Gal A residues, with the result that the molecular weight of LM pectins is typically significantly less than the molecular weight its parent HM pectin. Once formed, pectic acids and LM pectins are relatively more resistant to loss of molecular weight at neutral and alkaline conditions since, there are only limited numbers of methyl ester groups, or none at all, so that β-elimination-cleavage of the polymer chains slows down.

Both HM and LM pectins form gels. However, these gels form via totally different mechanisms (Voragen et al, In *Food polysaccharides and their applications*. pp 287-339. Marcel Dekker, Inc. New York, 1995). HM pectin forms a gel in the presence of high concentrations of certain co-solutes (for example sucrose) at low pH. HM pectins are typically not reactive with calcium or other multivalent ions and therefore do not form a calcium gel as do the LM pectins (infra). However, certain HM pectins can be made calcium-reactive by a block wise de-esterification process, while still having a DM of >50%. See, Christensen et al. U.S. Pat. No. 6,083,540.

LM pectins, which have high percentages of un-esterified carboxylic acid and/or carboxylate groups, are known to form gels in the presence of sufficient concentrations of calcium cations. The calcium ions are believed to coordinate to anionic carboxylate groups of the Gal A polymer subunits, and thus, are known as "calcium-reactive." The calcium-LM pectin gel network is believed to be built up by formation of what is commonly referred to as "egg-box" junction zones in which $Ca^{++}$ causes the coordination and cross-linking of complementary carboxylate groups along two complementary stretches of polygalacturonic acid polymer chains. Calcium-LM pectin gel formation is influenced by several factors, including the DM, ionic strength, pH, and molecular weight of the pectin (Garnier et al., *Carbohydrate Research* 240, 219-232, 1993; 256, 71-81, 1994). Current commercial LM pectins typically have a molecular weight of $7-14 \times 10^4$ Da and a Gal A content of ~75% (Voragen et al, In *Food polysaccharides and their applications*. pp 287-339. Marcel Dekker, Inc. New York, 1995). Typical pectins have a rhamnose content of <2%.

Pectins are typically utilized in the food industry and classified by the FDA as "GRAS" (Generally Regarded As Safe). They have also long been used as colloidal and anti-diarrhea agents. Recently, pectins have been utilized in the areas of medical device and drug delivery (Thakur et al., *Critical Reviews in Food Science & Nutrition* 37, 47-73, 1997). In the case of drug delivery, pectin has found its presence in many experimental formulations for oral drug delivery to the colon because pectin is readily degraded by bacteria present in this region of the intestines. The pectin is either used directly with no gelation involved, or a pectin calcium gel is pre-formed to encapsulate the drug agent before administration. Ashford et al., *J. Controlled Release* 26, 213-220, 1993; 30, 225-232, 1994; Munjeri et al., *J. Controlled Release* 46, 273-278, 1997; Wakerly et al., *J. Pharmacy & Pharmacology* 49, 622-625, 1997; *International Journal of Pharmaceutics* 153, 219-224, 1997; Miyazaki et al., *International Journal of Pharmaceutics* 204, 127-132, 2000.

U.S. Pat. No. 6,432,440 recently disclosed the use of LM pectins in liquid pharmaceutical formulations adapted to gel on contact with mucosal surfaces. U.S. Pat. No. 6,342,251 disclosed the use of a wide variety of polymers, including pectins in liquid and solid formulations for nasal administration of drugs suitable for the treatment of erectile disfunction. U.S. Pat. Nos. 5,707,644 and 5,804,212 recently disclosed the use of many polymers, including pectins, in formulating bioadhesive microspheres for the delivery of pharmaceuticals, peptides, and antigenic vaccines to nasal surfaces, but did not suggest the use of LM pectins or calcium induced gellation on contact with the nasal surfaces. The entire descriptions of U.S. Pat. Nos. 6,432,440, 5,707,644 and 5,804,212 are hereby incorporated herein by this reference, in their entireties, for their teachings regarding the formulation of in-situ gelling pharmaceutical compositions, the pectins used to prepare such compositions, and the administration of the compositions to animals and humans.

Biotechnology and associated methods for delivering drugs and related biopharmaceutical agents has been a subject of intense studies over recent years, but only limited progress has been made in the area of delivery of these agents, especially biopharmaceutical agents. Biopharmaceutical agents, such as peptides, proteins, nucleic acids, vaccines, antigens, and bioengineered cells, microorganisms, and viruses tend to be unstable, both in storage and after application. Injection of such agents into the tissues of an animal or human is sometimes successful, but is often economically and aesthetically undesirable, especially if frequent administrations are required. Many biopharmaceutical agents, especially the larger agents have in the past only been poorly absorbed if administered orally or to mucosal membranes. Once successfully administered to the animal, many biopharmaceutical agents are rapidly degraded by the body before they can effectively exert their desired function, and need protection from degradation and/or the benefits of time release formulations. Therefore, many long felt but as yet unfulfilled needs exist in the area of administration of biopharmaceutical agents.

Thus, a great need exists for a simpler, improved, and/or more efficient in-situ gelling compositions for drug and/or biopharmaceutical agent delivery.

SUMMARY OF THE INVENTION

The inventions disclosed herein relate to the delivery of physiologically active agents to the tissues or body fluids of animals, including humans. The inventions relate to methods of making and administering pharmaceutical compositions comprising polysaccharides, including pectins, that form an "in-situ" gel comprising the physiologically active agents when contacted with the tissues or body fluids. The compositions of the invention can be administered to the animal and its tissues and body fluids in the form or liquids, or solids, or powders comprising microspheres or microparticles of selected size ranges.

The compositions can be formulated to improve the stability and/or storage life of sensitive biopharmaceuticals including peptides, proteins, antigens, vaccines, nucleic acids, viruses, whole cells or fragments thereof. The compositions can be administered by injection into body tissues, organs, or cavities, so as to contact body fluids such as blood or serum, or the compositions can be administered to the various mucosal surfaces of the body, including those of the oral/digestive tract, or the nasal and lung cavities. In some embodiments, administration of biomolecules such as vaccines, antigens, peptides, and/or proteins via in-situ gels formed in the nasal cavity can be advantageous.

In some aspects of the invention, inclusion of or co-administration of solid or gel inducing agents and/or compositions comprising divalent or multivalent cations in the compositions can provide improved gel formations. The in-situ gels, once formed can slow and/or modulate the release, or improve the bio-availability of the physiologically active agents.

The features and benefits of the present invention can be illustrated by the following embodiments of the present invention.

In one aspect, the invention relates to a solid pharmaceutical composition for administering a physiologically active agent to an animal comprising:
  a) one or more physiologically active agents in an amount effective to induce a physiological response in an animal; and
  b) one or more polysaccharides comprising subunits having anionic carboxylate or sulfate groups, and
  c) one or more solid polysaccharide gelling compositions comprising one or more pharmaceutically acceptable salts of a divalent or multivalent metal cation;

wherein the pharmaceutical composition is in a solid form that forms a gel when contacted with a tissue or body fluid of an animal.

In another aspect, the inventions relate to solid pharmaceutical compositions for administering a physiologically active agent to an animal comprising:
  a) one or more physiologically active agents; and
  b) one or more pectic substances, wherein the pharmaceutical composition is a solid capable of forming a gel when contacted with a tissue or body fluid of an animal.

In a related aspect, the invention provides a composition for the sustained release of a physiologically active agent in an animal, wherein the composition is in a dry form comprising:
  one or more physiologically active agents in an amount that exerts a physiological response in the body of an animal; and
  a pectic substance having a degree of methylation less than 30% and an average molecular weight of greater than $1 \times 10^5$ Daltons, in an amount effective to form a gel when the composition is contacted with a tissue or body fluid of the animal.

The invention also relates to methods for making the compositions of the invention. In one such aspect, the invention relates to a method for preparing a dry composition for the sustained release of a physiologically active agent in an animal, comprising dissolving a mixture of a pectic substance and a physiologically active agent in a carrier to give a solution or dispersion, wherein the amount of the pectic substance is effective to gel in situ in the animal; and removing volatile components in the carrier to give the dry composition.

The invention also relates to methods for administering solid or liquid pharmaceutical compositions that will gel on contact with the tissues or body fluids of an animal In one aspect, the invention relates to a method comprising administering to a tissue or body fluid of an animal, in any order or combination, the following components,
  a. one or more physiologically active agents in an amount effective to induce a physiological response in an animal;
  b. one or more polysaccharides comprising subunits having anionic carboxylate or sulfate groups, and
  c. one or more solid gel inducing compositions comprising one or more pharmaceutically acceptable salts of a divalent or multivalent metal cation;
  to form a gel in contact with the tissue or body fluids of the animal.

In the embodiment described immediately above, the a, b, and c components can be administered in any order, and the a and b components may be in the form of either a solid or a liquid solution, and any combination or sub-combination of the a, b, and c components may be administered simultaneously or in mixtures.

The invention also relates to liquid compositions that are capable of gelling when contacted with the tissues of body fluids of an animal, and methods for applying the compositions to the tissues and body fluids. In one such aspect, the invention relates to a method for administering a physiologically active agent to an animal, comprising:
  a) providing a liquid solution or dispersion comprising
    i) liquid carrier,
    ii) a pectic substance having a degree of methylation of less than 30% and an average molecular weight of greater than $4.6 \times 10^5$ Daltons, in an amount effective to gel the liquid solution or dispersion when applied to the tissues or body fluids of the animal, and
    iii) one or more physiologically active agents; and
  b) applying the liquid solution or dispersion to the tissues or body fluids of the animal to form a gel comprising physiologically active agent in contact with the tissues or body fluids.

In some other aspects, the invention relates to a methods for administering vaccine composition to an animals or a humans, in either solid or liquid forms, comprising administering the vaccine composition to the mucosal surfaces of the animal or human. In one such aspect the invention relates to a method for administering a solid pharmaceutical composition comprising
  a) one or more powders comprising microspheres or microparticles that separately or together comprise
    i) a pectic substance having a degree of methylation less than about 30% and an average molecular weight of greater than $1 \times 10^5$ Daltons, in an amount effective to form a gel when the composition is contacted with the mucosal surfaces of an animal;
    ii) one or more antigens selected from the group consisting of a peptide, a protein, a nucleic acid, a live cell, a dead cell or a portion thereof, or a virus, in an amount that is capable of inducing an active immune response in the animal; and
  b) administering the powder to the nasal tissues and/or nasal fluids of the animal to form a gel in contact with the tissues or body fluids, and
  c) inducing an active immune response to one or more of the antigens in the animal.

The foregoing discussion has outlined some of the more pertinent features of the present invention. These should be construed to be merely illustrative of some of the more prominent features and applications of the invention. Accordingly, a fuller understanding of the invention may be had by referring to the following Detailed Description.

BRIEF DESCRIPTION OF THE DRAWINGS

For a more complete understanding of the preferred embodiment of the present invention, reference is made to the following detailed description taken in conjunction with the accompanying drawings, wherein like numerals refer to like elements, wherein:

FIG. 6a shows results for an LM pectin, and FIG. 6b shows results for a LMW *aloe* pectin. The diameter of the diffusion circle around the formulation placed in the normal calf serum was measured over time, as described in Example 17.

DETAILED DESCRIPTION

Figure 1:
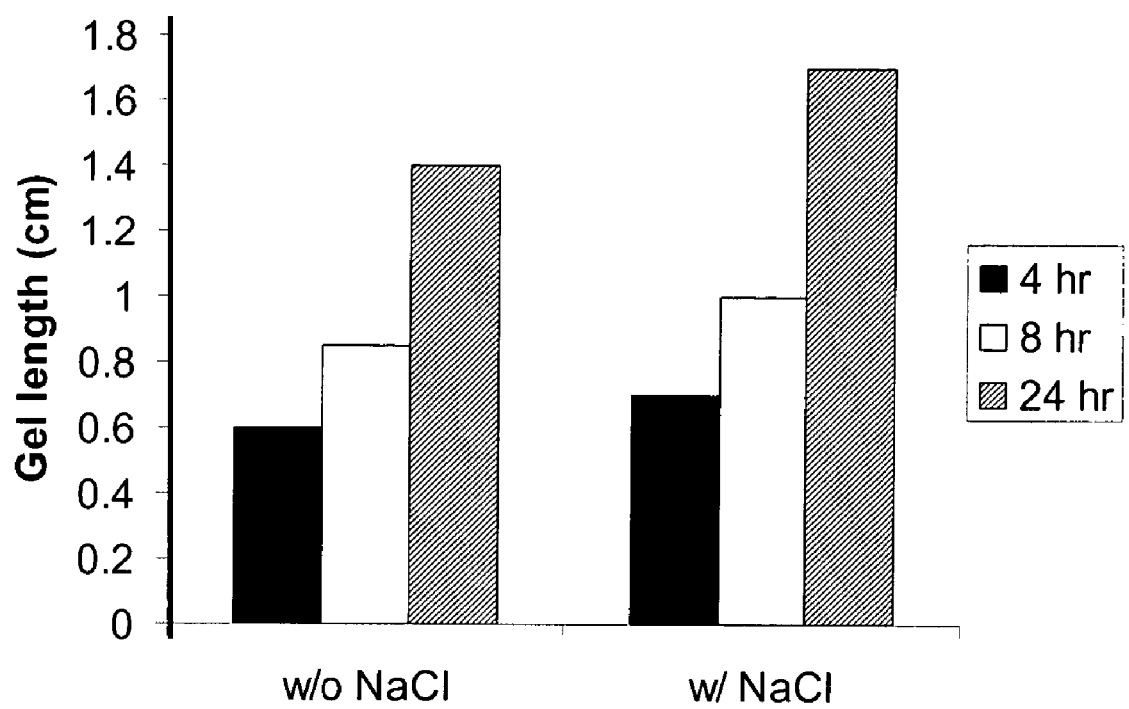
FIG. 1 is a bar graph representing the relationship of NaCl to the calcium gelation of *Aloe* pectin.

The present invention can be understood more readily by reference to the following detailed description of various embodiments of the invention and the Examples included therein and to the Figures and their previous and following description. Before the present compounds, compositions, and/or methods are disclosed and described, it is to be understood that this invention is not limited to specific starting materials, pharmaceutical agents or specific synthetic methods unless otherwise specifically indicated, as such can, of course, vary. It is also to be understood that the terminology used herein is for the purpose of describing particular embodiments only and is not intended to be limiting.

Definitions

In the specification and Formulae described herein the following terms are hereby defined.

"Optional" or "optionally" means that the subsequently described event or circumstance may or may not occur, and that the description includes instances where said event or circumstance occurs and instances where it does not. For example, the phrase "optional excipient" means that the excipient may or may not be included in the composition.

It must be noted that, as used in the specification and the appended claims, the singular forms "a," "an" and "the" include plural referents unless the context clearly dictates otherwise. Thus, for example, reference to "an aromatic compound" includes mixtures of aromatic compounds.

Often, ranges are expressed herein as from "about" one particular value, and/or to "about" another particular value. When such a range is expressed, another embodiment includes from the one particular value and/or to the other particular value. Similarly, when values are expressed as approximations, by use of the antecedent "about," it will be understood that the particular value forms another embodiment. It will be further understood that the endpoints of each of the ranges are significant both in relation to the other endpoint, and independently of the other endpoint.

By "pharmaceutically acceptable" is meant a material that is not biologically or otherwise undesirable, i.e., the material can be administered to an individual along with the relevant active compound without causing clinically unacceptable biological effects or interacting in a deleterious manner with any of the other components of the pharmaceutical composition in which it is contained.

By the term "effective amount" of a compound as provided herein is meant a sufficient amount of the compound to provide the desired regulation of a desired function, such as gene expression, antigen induced immune reaction, protein function, or a disease condition. As will be pointed out below, the exact amount required will vary from subject to subject, depending on the species, age, and general condition of the subject, the severity of the disease that is being treated, the particular agent used, its mode of administration, and the like. Thus, it is not possible to specify an exact "effective amount." However, an appropriate effective amount can be determined by one of ordinary skill in the art using only routine experimentation.

A "Gel" as the term is defined and used herein is an elastic solid or deformable semi-solid comprising a porous three dimensional network of organic polymer molecules containing within the network a reversibly absorbed liquid. In the context of the present invention, the reversibly absorbed liquid typically comprises the liquid water, although other liquid materials may also be present. In the context of the present invention, the network of polymer molecules typically comprise polysaccharides having repeat units comprising carboxylate or sulfate groups, including pectins. In many embodiments, at least some of the carboxylate or sulfate groups of the polysaccharide chains coordinate to divalent or multivalent cations such as calcium or aluminum, to form a cation crosslinked three dimensional network of polysaccharide molecules.

Gellation, as the term is used herein, refers to the formation of a gel that involves the formation of the polymer network and absorption of the liquid. In-Situ gels are formed from suitable precursor polymers and water, on or after contact with a tissue or body fluid, or a simulated tissue or body fluid.

A "Polymer" is a macromolecule formed by the covalent boding together of more than 10 divalent or multivalent subunits that are typically called monomers. The polymers of the present invention comprise both natural polymers such as proteins, nucleic acids, polysaccharides, and the like, which may contain a relatively large number of different types of monomers, or man-made polymers such as polyacrylates that often only contain one or a small number of different monomers.

A "Gel-inducing agent" is an agent capable of causing a polymer or a polymer solution to form a gel. Gel inducing agents often induce gel formation by inducing crosslinking between polymer chains, which in the context of the present invention include salts of divalent and multivalent cations, which can crosslink carboxylate or sulfate substituent groups on the same or differing polysaccharide molecules.

An "Ionic polymer" is a synthetic or natural polymer having monomers that have functional groups that is ionized or can be readily ionized (such as a carboxylic acid or the corresponding carboxylate group, or an organic sulfonic acid, and it corresponding organic sulfonate anionic group.

An "Ionotropic gel" is a gel formed by the crosslinking of a polymer with an ion. "Dried pharmaceutical preparation", a dried pharmaceutical formulation with a moisture content less than 20% in the form of powder, pad, film, sponge, tablet, or capsule.

A "powder" is solid, dry material that primarily comprises very small solid particles or spheres. The largest dimension of the bulk of the particles or spheres of a powder are less than a milimeter. In the context of the above definition, "dry" means that there is very little, if any free flowing liquid (including water) on the surface of the powder particles or spheres that would tend to significantly inhibit the normally free-flowing physical characteristics of a powder. The powders of the current invention may in fact comprise absorbed water within polymer networks, but do not comprise significant amounts of flowable liquid water on their surfaces.

A "microsphere" is a small, approximately spherically shaped solid particle having a generally continuously curved and non-angular surface, the particle having effective diameters between about 0.1 and about 250 microns (µM). Microspheres, as defined herein include microcapsules. A "microparticle" in contrast to a microsphere, has a flat, angular, rhombohedral, or irregular surface. Microparticles have a longest linear dimension of between about 0.1 and about 250 microns.

A "physiologically active agent" refers to an agent, compound, or composition that can induce a physiological response in the body of an animal. Physiologically active agents include nutrients, small molecule drugs and therapeutic agents, large molecule drugs and therapeutic agents, a pharmacologically active substance; a diagnostic agent; a therapeutic agent; a nucleic acid; a peptide; a polymer; a small protein; a large protein; and a live cell. A pharmacologically active substance includes a substance that illicits immune response, such as a vaccine. Examples of therapeutic agents include anti-bacterial substances, antimicrobial agents, antiparasitic agents, antibiotics, antihistamines, decongestants, antimetabolites, antiglaucoma agents, anti-cancer agents, antiviral agents, anti-fungal agents, anti-inflammatory agents, anti-diabetic agents, anesthetic agents, anti-depressant agents, analgesics, anti-coagulants, opthalmic agents, angiogenic factors, immunosuppressants, and anti-allergic agents.

A "Vaccine" comprises one or more antigens, in the form of a protein, a carbohydrate, a lipid, or nucleic acid, a cell in whole or part, a virus, etc., that is capable of inducing immune response in a treated organism, against the antigen or the microorganism or tissue from which it is derived, so as to treat or prevent diseases caused by microorganisms, viruses, and/or or cancer.

The term "pectic substance," as used in this invention, includes any material comprising a major proportion of one or more polysaccharide materials derived from a naturally occurring pectin. Pectic substances include low and high methoxyl pectins, de-esterified pectin, pectin calcium gel, *Aloe* pectin sodium gel, pectic acid, pectate, pectinic acid, pectinate, protopectin, and pectin-rich substances, such as *Aloe vera* inner gel cell wall fiber, individually, collectively, or in combination thereof. As discussed above, pectin is a group designation for those complex colloidal carbohydrate derivatives which occur in, or are prepared from, plants and contain a large proportion of anhydrogalacturonic acid monomeric units.

A "de-esterified" pectin is a pectin from which a plurality of methyl ester groups have been removed from the pectin polymer by an artificial process.

A "Pectic acid" is the group designation applied to pectic substances mostly composed of colloidal polygalacturonic acids and essentially free from methyl ester groups. A totally de-esterified pectin is a pectic acid or polygalacturonic acid. "Pectates" are either normal or acid salts of pectic acids. "Pectinic acids" are the colloidal polygalacturonic acids containing more than a negligible proportion of methyl ester groups. "Pectinates" are either normal or acid salts of pectinic acids. "Protopectin" is applied to the water-insoluble parent pectin which occurs in plants and which upon restricted hydrolysis yields pectins, pectinic acids, and others. The water-insoluble pectin may be associated with the cellulose present in the plant, such as the *Aloe vera* inner gel or rind cell wall fiber.

A residue of a chemical species, as used in the specification and concluding claims, refers to a structural fragment, or a moiety that is the resulting product of the chemical species in a particular reaction scheme or subsequent formulation or chemical product, regardless of whether the structural fragment or moiety is actually obtained from the chemical species. Thus, an Gal A residue in a pectin refers to one or more of the galuronic acid monomeric repeat units in the pectin, regardless of whether galuronic acid itself is present in or was used to prepare the pectin.

In the subsequent description, reference is frequently made to units of "% (w/v)". By this expression the "% (w/v)" is defined to be the number of grams of substance in 100 ml of a liquid solution. In dilute aqueous solutions, the density of the liquid will be approximately 1 gram per milliliter, so that the "% (w/v)" would be approximately equal the number of grams of solid in 100 grams of liquid. In these "% (w/v)" units, a solution that was 1% (w/v) would correspond to 1 gram per 100 mililiters, =1 gr/100 ml=10 mg/ml.

Abbreviations Used Herein Include:

CMC, carboxylmethyl cellulose; Da, dalton; DM, degree of methylation; Gal A, galacturonic acid; HEC, hydroxyethyl cellulose; HM, high methoxyl; HPMC, hydroxypropylmethylcellulose; kDa, kilodaltons; LM, low methoxyl; PBS, phosphate buffered saline; PEG-PLGA-PEG, polyethylene glycol-poly(lactic-co-glycolic acid)-polyethylene glycol; PEO-PLLA, poly(ethylene oxide)-poly(L-lactide); PEO-PPO-PEO, poly(ethylene oxide)-poly(propylene oxide)-poly(ethylene oxide).

Pharmaceutical Compositions

In some embodiments, the invention relates to a solid pharmaceutical composition for the delivery of a physiologically active agent to an animal comprising:

a. one or more physiologically active agents in an amount effective to induce a physiological response in an animal;

b. one or more polysaccharides comprising subunits having anionic carboxylate or sulfate groups, and c. one or more solid, polysaccharide gel inducing compositions comprising one or more pharmaceutically acceptable salts of a divalent or multivalent metal cation;

wherein the pharmaceutical composition is in a solid form that forms a gel when contacted with a tissue or body fluid of an animal.

The above-described solid pharmaceutical composition is a solid of any solid form, including a pad, a tablet, a capsule or a powder. In many embodiments the solid pharmaceutical composition is formulated in the form of a powder. The powders can be present as a plurality of microparticles and/or microspheres, as the terms are defined elsewhere herein. In practice, powders having desired ranges of particle size can be produced by any of many methods well known the art, including emulsion processes, encapsulation processes, spray drying processes, grinding of solids, etc. In a final step of many processes, precursor solids or powders are passed through one or more sets of sieves. Such sieves have openings of defined and desirable sizes, for example, 250, 200, 150, 100, 80, 60, 50, 40, 30, 20, 11, 10, 9, 5, 1, and 0.1 µM, so as to produce a variety of ranges of particle sizes for the powders, microparticles and/or microspheres. Desirable ranges of particle sizes can include the approximate ranges of particle sizes disclosed in Table 1 below. In one embodiment, the opening of the sieves permit the powders, microparticles or microspheres to pass through so as to have size of about 250 µM, or less. Optionally that powder can then be processed with another smaller sieve to remove the smallest particles, so as to produce a solid composition having particle sizes between, for example, about 11 µM and about 250 µM.

There can also be beneficial effects to certain other constraints on particle size distributions. Accordingly, in some embodiments a specified percentage of the particles of a solid composition will fall inside the specified size range. For example, it could be desirable that about 80%, or about 85%, or about 90%, or about 95% of the particles fall within a specified particle size range. To cite one example, in some embodiments, the solid compositions of the inventin comprise microspheres, and less than 90% of the microspheres have a diameter between 0.1 and 10 µM.

The one or more polysaccharides employed in the invention can be either neutral or anionic, because they comprise monosaccharide subunits having anionic carboxylate or sulfate groups. It is to be understood that the anionic carboxylate groups can be in the form of either a salt of carboxylic acid attached to the monomeric subunits, or the parent carboxylic acid itself, which is readily ionizable or ionized at physiological pH. Similarly, the anionic sulfate groups of the monosaccharide subunits include both a salt of a monosaccharide comprising a sulfonic acid group and a monomeric subunit comprising the acid form of the sulfate. A variety of polysaccharides comprise anionic carboxylate or sulfate groups, including carboxylated starches, pectic substances, an alginate, a carrageenan, or a gellan.

TABLE 1

Selected Compositional Ranges* for Components of the Gel-Forming Compositions of the Invention

| Dried formulations (% w/w) | Liquid formulation |
|---|---|
| Polysaccharides | |
| 0.0001 to 99% | 0.001 to 20 (% w/v) |
| 0.001 to 50% | 0.01 to 10 |
| 0.005 to 20% | 0.05 to 8 |
| 0.01 to 10% | 0.1 to 4 |
| Pharmaceutically Active Agent | |
| 0.0001 to 90% | 0.001 to 50 (% w/v) |
| 0.001 to about 70% | 0.01 to 25 |
| 0.01 to 50% | 0.05 to 10 |
| 0.1 to 20% | 0.1 to 8 |
| Powder, Microsphere, or Microparticle Particle Size | |
| 0.1 µm to 300 µm | n/a |
| 1 µm to 200 µm | n/a |
| 10 µm to 100 µm | n/a |
| 12 µm to 60 µm | n/a |
| 15 µm to 50 µm | n/a |
| Pharmaceutically Acceptable Thickeners | |
| 0.01 to 90% | 0.01 to 10(% w/v) |
| 0.1 to 80% | 0.1 to 8 |
| 1.0 to 70% | 0.2 to 6 |
| 5.0 to 50% | 0.5 to 5 |
| Pharmaceutically Acceptable Excipients | |
| 0.1 to 90% | 0.1 to 40(% w/v) |
| 1.0 to 50% | 0.5 to 30 |
| 2.0 to 30% | 1.0 to 20 |
| 3.0 to 20% | 2.0 to 10 |
| Divalent or Multivalent Metal Cations | |
| 0.01 to 80% | 0.00001 to 0.05(% w/v) |
| 0.05 to 40% | 0.0001 to 0.02 |
| 0.1 to 10% | 0.001 to 0.01 |

*Although shown pairwise in the table above, it is expressly contemplated herein that any of the endpoints recited for a particular category of components cited in the table may be combined with any of the other corresponding endpoints recited for that category of component, to form a new range for that category of components.

In many embodiments, the solid pharmaceutical compositions comprise one or more pectins, either in its acid form or in the form of a salt of the carboxylic acid. The general structure and characteristics of pectins have been described hereinabove. In some embodiments the pectins have a degree of methylation (DM) of equal to or less than about 70%, 50%, 30%, 25%, 20%, 19%, 18%, 15%, 14%, 12, 10%, 9%, or 5% Lower degrees of methylation typically, but not always lead to improved gellation properties, though many other factors are involved in determining the gellation properties of the pectins.

The molecular weight of a pectic substance or a pectin is an important factor in its gellation properties, higher molecular weights typically producing better gellation properties. The importance of molecular weight in the gellation of pectins is described in U.S. Pat. No. 5,929,051, which is hereby incorporated herein by this reference, it its entirety, for its teaching of the characteristics of pectins and *aloe* pectins. In many embodiments, the pectic substances or the pectins have an average molecular weight of greater than about $4.6 \times 10^5$ Daltons, or about $5.0 \times 10^5$ Daltons. Alternatively, the pectic substances or pectins may have an average molecular weight of equal to or less than about $2 \times 10^5$ Daltons, $3 \times 10^5$ Daltons, $4 \times 10^5$ Daltons, $6 \times 10^5$ Daltons, $7 \times 10^5$ Daltons, $8 \times 10^5$ Daltons, or $9 \times 10^5$ Daltons. In some embodiments, the pectic substances or pectins have a molecular weight greater than $1 \times 10^6$ Daltons and a degree of methylation of less than 10%.

The compositions of the invention (liquid or solid) can comprise one or more physiologically active agents, as that term is defined elsewhere herein. In some embodiments, the physiologically active agents can include a therapeutic agent, a diagnostic agent, a carbohydrate, a lipid, a peptide, a nucleic acid, a live cell, a dead cell in whole or part, a microorganism in whole or part, a virus in whole or part, a vaccine, an antigen, and a protein. The compositions of the invention can comprise therapeutic agents such as small molecule drugs. In many embodiments the compositions of the invention can comprise a wide variety of larger biological agents including molecules, cells, viruses, antigens, etc. In some embodiments, the physiologically active agents can preferably include peptides, proteins, vaccines and/or antigens, live cells, dead cells in whole or in part, or viruses in whole or in part.

The biological agents employed in the invention tend to be significantly less stable, both in storage and during and after application, than other materials. The compositions of the present invention can be unexpectedly superior in terms of the stabilization and storage of such biological agents. In particular, when mixed with an appropriate gelling polysaccharide, especially pectins, and dried to form a solid, the polar character of the polysaccharide and the low water content of the solid composition can significantly prolong the shelf life a biological molecule that might otherwise be unstable in an aqueous solution stored at room temperature. Moreover, once incorporated into an in-situ gel after application to tissues or body fluids, the large biological agents tend to be stabilized by the polysaccharide matrix, and tend to be released from the gel more slowly than smaller compounds, so as to achieve a high degree of bioavailability, but with a desirable slow release rate. These desirable characteristics of the compositions of the invention can be particularly important in the administration of vaccines and the associated antigens.

The solid compositions of the invention can comprise small amount of water, especially those comprising pectins, which tend to have residual water absorbed with the pectins. Therefore, the solid compositions of the invention may comprise about 20% water by weight, or about 15%, 12%, 10%, 9%, 8%, 7%, 6%, 5%, 3%, 2% 1%, or less. At any of the percentages of water described above the particles can typically be described as "dry," in the sense that no free flowing liquid is apparent on the surface of the particle so as to cause significant stickiness that would significantly impede the free flow of the solid in the form of a powder. Lower percentages of water by weight are preferred in some embodiments of the invention, so as to improve the stability of the physiologically active agents during storage, or to improve the physical characteristics of the solid.

In another aspect, the invention relates to a method for delivering a physiologically active agent to an animal comprising administering to a tissue or body fluid of an animal, in any order or combination, the following components,
- a. one or more physiologically active agents in an amount effective to induce a physiological response in an animal;
- b. one or more polysaccharides comprising subunits having anionic carboxylate or sulfate groups, and
- c. one or more solid gel inducing compositions comprising one or more pharmaceutically acceptable salts of a divalent or multivalent metal cation;

to form a gel in contact with the tissue or body fluids of the animal.

In the above-described methods, components a, b, and c can be administered in any order, combination, or physical form so long as component c is administered as a solid, and a gel is formed in contact with the tissues or body fluids of the liquid. In some embodiments of the method, components a, b, and c are administered as components of a powder composition, wherein the components can be in the form of a physical mixture of one or more solid phases. In some embodiments, solid component c is present as a distinct solid phase comprising powder particles, while in other embodiments solid component c may also be present in a mixture on the molecular level with the physiologically active agent.

In some embodiments, components a and b are administered as separate or mixed powders, while component c is present a different and chemically distinct solid phase. For example, components a and b can be administered as a physical mixture of one or more powders comprising component a, and one or more powders comprising component b, which may be administered separately from or together with component c.

In some favorable embodiments, components a and b are administered as a solid composition prepared by dissolving one or more physiologically active agents and one or more polysaccharides in a liquid carrier, and then removing sufficient liquid carrier to form a solid mixed composition, wherein the agent and the polysaccharide are intimately intermixed on the molecular level. Component c can be administered before, concurrently with, or after the administration of the solid mixed composition, which is often administered in the form of a powder.

In some other embodiments, components a and b are administered as a solution in a liquid carrier, while component c is administered as a separate solid.

In another embodiment, the invention relates to a composition for the administration of a physiologically active agent to an animal comprising:
- a. one or more physiologically active agents in an amount effective to induce a physiological response in an animal; and
- b. one or more pectic substances having a degree of methylation less than about 30% and an average molecular weight of greater than about $1 \times 10^5$ Daltons, wherein the composition is a solid capable of forming a gel when contacted with a tissue or body fluid of an animal.

In another embodiment, the invention relates to a method for sustained release of a physiologically active agent to an animal, comprising:
- a) providing a liquid solution or dispersion comprising
  - i) a liquid carrier,
  - ii) a pectic substance having a degree of methylation of less than 30% and an average molecular weight of greater than $4.6 \times 10^5$ Daltons, in an amount effective to gel the liquid solution or dispersion when applied to the tissues or body fluids of the animal, and
  - iii) one or more physiologically active agents; and
- b) applying the liquid solution or dispersion to the tissues or body fluids of the animal to form a gel comprising physiologically active agent in contact with the tissues.

In some embodiments of the above methods of applying liquid compositions, the pectic substance can be an *aloe* pectin, whose beneficial characteristics have been described. In related embodiments of the above methods of applying liquid compositions, the physiologically active agent is a biological agent such as a peptide, a protein, an antigen, a vaccine, a live cell, a dead cell in whole or in part, or a virus in whole or in part. In related embodiments, the tissue or body fluid can be a mucosal surface, including a nasal mucosal surface.

In the above methods of applying liquid compositions, the compositions can be modified with certain agents so as to improve their storage characteristics. As further described in Example 25 and elsewhere herein, salts of monovalent cations such as sodium chloride and/or ammonium chloride, or buffering agents such as phosphate buffers can be added to the liquid composition to provide a solution of physiological pH, and ionic strength. Moreover, such solutions have some unexpectedly superior properties when employed for first storing and then applying the physiologically active agents. If NaCl or $NH_4Cl$ are added at appropriate concentrations to liquid solutions comprising the pectins and agents, the solution can reversibly form a gel when refrigerated for storage (at around 4° C.). The gel so formed can stabilize and protect sensitive biological active agents from precipitation and/or decay. When the composition is removed from storage for administration to the animal or human, the gel dissolves leaving a clear and precipitate free solution that is suitable for administration by injection, to mucosal surfaces, and the like.

Moreover, small amounts of salts of divalent cations can be added to the liquid solutions without gelling them, as is described in Example 24, with the benefit that when the modified solution is applied to a tissue or body fluid, in-situ gelation is enhanced.

Additionally, the liquid solutions can comprise the other thickeners and/or excipients described elsewhere herein.

As described above, some embodiments of the invention relate to compositions and methods for administering vaccines and/or antigens to animals and/or humans. Therefore, in some embodiments, the invention relates to method for administering a vaccine to the nasal mucosa of an animal, comprising administering to the mucosal surfaces of the animal:

a. one or more powders comprising microspheres or microparticles that separately or together comprise
   i) one or more polysaccharides comprising subunits having anionic carboxylate or sulfate groups, in an amount effective to form a gel when the composition is contacted with the mucosal surfaces of an animal;
   ii) one or more antigens selected from the group consisting of a peptide, a protein, a nucleic acid, a live cell, a dead cell or a portion thereof, or a virus, in an amount that is capable of inducing an active immune response in the animal; and
b. administering the powder to the nasal tissues and/or nasal fluids of the animal to form a gel in contact with the tissues or body fluids, and
c. inducing an active immune response to one or more of the antigens in the animal.

Nasal administration of vaccines is of particular interest, because of the many advantages of such administrations. Nasal administration typically avoids the discomfort and cost associated with injection, and also avoids the typically destructive effect of the acids and enzymes of the digestive tract on sensitive antigens. Nevertheless, nasal administration of vaccines can be challenging, because the nasal mucosal surfaces are well known to rapidly renew themselves and clear foreign agents over very short time periods. Therefore many prior art attempts at the nasal administration of vaccines have not achieved therapeutic success, due to rapid clearance of the vaccine components from the nasal mucosa, so that insufficient time and contact is maintained so as to effectively induce a desired level of immune response in the animal.

The current invention provides compositions and methods of administering those compositions that unexpectedly overcome the problems of the prior art, by providing compositions that form in-situ gels comprising the antigens that adhere to the nasal mucosal surfaces, and provide extended residence times for the antigen components of the vaccines. See Example 26, and FIG. 10. As shown by Examples 22 and FIG. 8, the result is an unexpectedly improved and superior induction of an active immune response in the animal.

In many embodiments, after administration of the vaccine and/or antigens to the nasal mucosa of the animal the immune response of the animal can increase by more than about 10%, as measured by the IgA levels in the lung washings of an animal as compared to the IgA levels obtained in a control experiment that administers a control composition that does not comprise the polysaccharide. Preferably, the immune response of the animal will increase by more than about 25%, 50%, 75%, 100%, 150%, or 200%, as measured by the IgA levels in the lung washings of an animal as compared to the IgA levels obtained in a control experiment that administers a control composition that does not comprise the polysaccharide.

It is realized that one unique advantage of the powder formulation with gel forming ionic polymers is the ability to blend the powder formulation with a dried gel-inducing agent to ensure a consistent gel formation after administration. Thus, a gel inducing agent made as a dried powder may be added to the powder formulation. Since the inducing agent is in a dry state, there will be no gel formation prior to delivery or hydration. After delivery, the gel-inducing agent is dissolved and thereby facilitates gelation of the formulation powder particles through interacting with the gelling ionic polymer.

For polymers like pectins, alginates, and polyphosphazene, the gel-inducing agent could be various 2+, 3+, and other multi-valent metal ions. Examples of these ions include calcium, zinc, magnesium, ferric, and aluminum. They may be prepared as a powder by themselves or in the presence of an excipient. The inducing agent powder particle density and size may be adjusted to allow it to be mixed with the active agent formulation powders in a consistent and homogenous manner.

In addition, other groups of pharmaceutically acceptable excipients may be used, including binders, fillers or bulking agents, lubricants, flavoring agents, and taste masking agents. Binders are use to generate a free-glowing powders; fillers are used to increase the powder bulk; lubricants are used to increase the flow of a powder; taste-masking agents are used to reduce the unpleasant taste of a medicine.

*Aloe* Pectin

*Aloe* pectins are isolated from *Aloe vera* plant as recently described in U.S. Pat. No. 5,929,051, the entire content of which is incorporated herein by reference. *Aloe* pectins are naturally a LM pectin and capable of calcium gelation. In addition, *aloe* pectins can possesses several unique chemical properties that are particularly related to gelation, including high molecular weight ($>1\times10^6$ Da), a high Gal A content (>75%, 80%, 85%, and in many cases >90%), and a low DM (<10%). A DM below 10% makes *Aloe* pectin almost pectic acids, but with a significantly higher molecular weights than other commercially available low DM pectins and pectic acids, as illustrated in Example 27, Table 8. *Aloe* pectins also have a significantly higher percentage of carboxylate groups in the polymer as compared to other pectins, because of their high GalA content. *Aloe* pectins also typically have a desirably high degree of branching in the polysaccharide backbone, and an unusually flexible polymer backbone, as a result of their high rhamnose contents, which can be >3% or greater than 4%, as compared to about 2% in other pectins. A pectin with such a low DM, a high molecular weight, and a high Gal A and rhamnose content had not been described previously to U.S. Pat. No. 5,929,051. *Aloe* pectin, which has recently become commercially available in purities suitable for pharmaceutical applications, is an off white powder and completely soluble in water as the finished commercial product, whereas previously commercially available and/or experimental LM pectins are yellow to tan powders that contain significant amount of insoluble materials, and thus are undesirable for pharmaceutical applications.

*Aloe vera* leaves consist of two parts, an outer green rind and a clear inner gel which is also referred to as pulp. *Aloe* pectin is extracted from the inner gel or outer rind cell wall fibers. Use of a chelating agent at a slight alkaline pH is found to be the most efficient extraction method. *Aloe* pectin is unique as compared to previously described pectins. It has a high rhamnose content of >4% in the purified pectin preparation which is at least 2 times higher than described in other pectins such as citrus, apple, sugar beet, and sunflower. Rhamnose is a key sugar in the pectin backbone whose content affects the flexibility of the molecule. *Aloe* pectin also possesses a rare sugar, 3-OMe-rhamnose which has not been described in any other pectins. *Aloe* pectin is naturally LM, having a DM generally <30% and can be as low as <10%. The Gal A content of *Aloe* pectin is >70% and can be as high as >90%. *Aloe* pectin is capable of gel formation in the presence of calcium. A monovalent cation, such as sodium, potassium and lithium accelerates the formation of gel.

*Aloe* pectin can be distinguished from other pectins by one or more of the following characteristics:
1. A high molecular weight (>1×10$^6$ Da) and a high intrinsic viscosity (>550 ml/g);
2. A high rhamnose content (>4%);
3. A high galacturonic acid content (>90%);
4. Containing 3-OMe-rhamnose;
5. Being naturally LM with a DM as low as <10%;
6. Capable of calcium gel formation;
7. Capable of monovalent cation-based gel formation at low temperature (4° C.).

We found that by injecting into a body or by topically applying to wound surfaces as a route of administration, a non-gelled liquid pectin can form a gel in-situ at the site of administration. The in-situ gel is firm and non-flowing just like the calcium gel formed in vitro, which is distinct from the hydrogel, a viscous but still flowing solution. The in-situ gelation of *Aloe* pectin was found to be particularly efficient such that the minimal *Aloe* pectin concentration needed for forming a firm solid in-situ gel is as low as 2.5 mg/ml or 0.25% (w/v) and can be even lower if a thickener is added.

Additionally, the capacity for monovalent cation gel formation can be advantageously applied to prepare compositions comprising sensitive biological molecules comprising sodium and/or ammonium chloride at physiological pH and ionic strength that will reversibly gel when refrigerated, so as to form a gel that can stabilize sensitive biological agents. The gels so formulated then redissolve when returned to room temperature to form clear, precipitate free liquid pharmaceutical composition, as described in Example 25. The redissolved solution can then be applied to tissues or body fluids by various methods of administration to form an in-situ gel.

The gel compositions can be made isotonic or iso-osmotic and adjusted to the pH of mammalian body fluids, such as lacrimal tears. The pH and osmotic pressure of such bodily fluids are 7.4 and 29 mOsm/kg, respectively. It is advantageous to deliver a pharmacologically active medicament to an area of the mammalian body requiring pharmacological treatment under desired pH and osmotic pressure conditions which, for instance, match those of bodily fluids. Optionally, the pharmaceutical compositions of the invention can be provided in a sterile condition.

Although not wanting to be bound by any theory, it is believed that the pectin in-situ gelation is primarily mediated by the calcium ions in the body fluids. Blood has a calcium concentration of 8.5-10.3 mEq/dl. The calcium gelation of pectins is enhanced in the presence of NaCl which is also a normal component of the body fluids. There are 134 mEq/L NaCl in the blood.

The in-situ gel also forms in the presence of various agents, including small organic compounds, proteins, nucleic acid, live cells, and other polymers following subcutaneous injection, demonstrating the capability of the pectin for delivering a wide range of agents in an encapsulated or entrapped form. When a poorly soluble compound such as silvadene was incorporated, the in-situ gel still formed. Once delivered, the pectin in-situ gel clearly exerted a slow release effect. This was demonstrated under in vitro as well as in vivo conditions with a small organic model compound (fast green). In addition, when bFGF is delivered with the pectin in-situ gel, a significantly increased cell proliferation surrounding the gel was observed.

*Aloe* pectin is more efficient than current commercial pectins including LM pectins, and polygalacturonic acid, and amidated LM pectins for in-situ gelation. A well-formed in-situ gel was only obtained with commercial polygalacturonic acid or LM pectin at a concentration 10 times higher than that for *Aloe* pectin. Current commercial LM pectins and polygalacturonic acids have a lower Gal A content (~75%), a much lower molecular weight (7-14×10$^4$ Da), and a DM of 15-50%. There are other polymers that can form a calcium gel. One example is alginate. However, alginate was not previously believed capable of forming a well defined in-situ gel at concentrations tested. Alginate is a polysaccharide block copolymer consisting of guluronic acid (G) and manuronic acid (M) (Moe et al., In *Food polysaccharides and their applications*. pp 287-339. Marcel Dekker, Inc. New York, 1995). These two residues in alginates exist as G-block, M-block, or alternating MG-block. Only the G-block is responsible for calcium gelation. The total G content varies widely dependent on the sources; the highest G content is ~70%. In addition, the alginate calcium gelation is inhibited by the presence of NaCl, which exists in the physiological fluids.

Several other polymers have also been shown to be capable of in-situ gelation. However, most of them require a high polymer concentration for in-situ gel formation (>20%) (Poloxamer, PEO-PLLA diblock copoly, PEG-PLGA-PEG triblock copolymer, cellulose and acetophalate latex). Some of these polymers are not biodegradable, such as Poloxamer, or require manipulation of the temperature before administration (PEO-PLLA diblock copolymer) or during formulation (Pluronics and Gelrite). The thermally gelling polymers (Poloxamer, Pluronics, PEO-PLLA diblock copolymer, PEG-PLGA-PEG triblock copolymer, and Matrigel) also have the disadvantage of gelling before administration due to ambient temperature changes during packaging or storage. Furthermore, many of these polymers form only a hydrogel, a viscous but still flowing solution (e.g., Poloxamer and Pluronics). In addition, some polymer formulations require two different polymers or the application of a second component for gelation to occur. Pectin, especially the *Aloe* pectin, is advantageous over these polymers or compositions in that the polymer concentration required to achieve the in-situ gelation is very low (χ0.25%, w/v) and can be even lower if a thickener is added. The preparation does not require temperature or pH adjustment, or application of a second component for the in-situ gelation to occur. The gel is transparent, and there is no dramatic increase in gel cloudiness beyond certain concentration ranges as with PEG-PLGA-PEG triblock copolymer and Pluronics.

The advancement of biotechnology is generating more and more protein-based therapeutics. Proteins are inherently unstable. Proper formulation and delivery are critical to their in vivo functions (Langer, *Nature* 392, 5-10, 1998; Putney and Burke, *Nature Biotechnology* 16, 153-157, 1998). The pectin in-situ gel is particularly suited for protein delivery because of its mild gelling conditions. Many protein agents are also intended to be delivered locally in a sustained manner, e.g., growth factors for wound healing and angiogenic factors for therapeutic angiogenesis. This can also be achieved with pectin in-situ gel. When bFGF was delivered with the *Aloe* pectin in-situ gel, a significantly increased cell proliferation surrounding the gel was observed.

Based on the weight of the final composition or formulation, the physiologically active agent can vary from about 0.01% to about over 90%. The amount of the physiologically active agent used would depend on the type, form, and nature of the physiologically active agent.

The range of the pectic substance can vary from about 0.01% to about 40%, based on the total weight of the composition, preferably from about 0.1% to about 20%, and more preferably from about 0.25% to about 2%. The amount of the pectic substance used would depend on the type, form, and nature of the physiologically active agent. Optionally, a carrier or excipient may be used.

A carrier used for this invention includes any pharmaceutically acceptable carrier, such as water; saline; a buffered aqueous solution; emulsion, such as oil/water emulsion; adjuvant; a wetting agent; tablet; and capsule. Based on the weight of the final composition or formulation, the carrier can vary from about 0% to about 90%. The amount of carrier present would depend on the physiologically active agent and the manner by which the formulation or composition is to be delivered.

Representative buffering agents include alkali or alkali earth carbonate, chloride, sulfate, phosphate, bicarbonate, citrate, borate, acetate, and succinate, and/or ammonium chloride. Representative preservatives include sodium bisulfite, sodium thiosulfate, ascorbate, benzalkonium chloride, chlorobutanol, thimerosal, phenylmercuric borate, paraben, benzylalcohol, and phenylethanol.

Thus, one embodiment of the current invention is to provide a composition for the sustained delivery of a physiologically active compound, and the composition contains a pectin and a physiologically active compound with or without a pharmaceutically acceptable thickener. Preferably, the composition changes from a liquid to a gel upon administration of the composition to the body of an animal, and thus the release of the physiologically active compound is sustained or controlled.

A biodegradable thickener such as polyvinylpyrrolidone ("PVP"), carboxymethylcellulose ("CMC"), hydroxyethylcellulose ("HPMC"), sodium alginate, collagen, gelatin, and hyaluronic acid may be added to the formulation. Addition of such a thickener does not influence the gelling efficiency as described below, but provides an advantage of enhancing the density of the gel matrix and the in-situ gel formation at lower pectin concentrations. In addition, polymers that are responsive to changes in pH, ionic strength, and temperature may also be used as long as they are synergistic with the pectin gelation. Furthermore, a blend of different pectins may be used with or without a thickener. Other thickeners include Carbopol, Gelrite, chitosan, and xyloglucan. Based on the weight of the final composition or formulation, the thickener can vary from about 0% to about 90%. The amount of biodegradable thickener used would depend on the physiologically active agent and the manner of which the composition or formulation is used.

Still another embodiment of the current invention is to provide a composition consisting of a pectin with or without a pharmaceutically acceptable thickener for use as a medical device.

Preferably, the pectic substance is calcium reactive, in that the carboxylate substituent groups of the galacturonic acid monomeric subunits of the pectin can react to coordinate calcium ions, and thereby form calcium crosslinked gels. The formation of such calcium reactive gels can be determined by various spectroscopic and/or wet chemical methods, including reaction of the crosslinked gels with calcium chelating agents, such as ethylenediamine-tetraacetic acid and its salts ("EDTA"), which can be used to remove the coordinated calcium from the gel and thereby cause dissolution of the gel.

More preferably, the pectic substance is a LM pectin or polygalacturonic acid. Still more preferably, the pectic substance is *Aloe* pectin.

A pectin in-situ gelling compositions containing a therapeutic or diagnostic agent(s) may be administered or delivered to the animal by various means. For example, it may be applied topically to the eyes, mucosal surfaces, or wounds. It may also be delivered parenterally, such as subcutaneously, intramuscularly, or via intraperitoneal injection. It may also be injected into an organ, a joint cavity, or a tumor.

Pectin can be extracted from many different plant sources. Besides citrus and apples, for example, pectin has also been obtained from potatoes, grape fruits, sugar beets, and sunflower heads. Pectin may be modified. For example, an amidated pectin is produced by treatment with ammonia. It is conceivable that an *Aloe*-pectin-like pectin may be present in a different plant species or a pectin from a different plant source may be produced, re-processed, and/or modified in a way to enhance the in-situ gelling ability based on the principles disclosed herein. Furthermore, although an LM pectin with a DM<50% is preferred for use in the present invention because of its calcium reactivity, certain HM pectins are also known to be calcium-sensitive and capable of forming calcium gel, and may therefore be used for in-situ gelling (Tibbits et al., *Carbohydrate research* 310, 101-107, 1998). In addition, a block wise de-esterified HM pectin that still has a DM of >50%, but is rendered calcium sensitive by the block wise de-esterification, may also be used. See, Christensen et al. U.S. Pat. No. 6,083,540.

Thus, it should be appreciated by those skilled in the art that the specific embodiments disclosed above may be readily utilized as a basis for modifying or designing other structures for carrying out the same purposes of the present invention. It should also be realized by those skilled in the art that such equivalent constructions do not depart from the spirit and scope of the invention as set forth in the appended claims and/or examples.

EXAMPLE 1

In-situ Gelation of *Aloe* Pectins

Extraction of *Aloe* Pectin

*Aloe* pectin was extracted from cell wall fibers prepared from either pulp or rind of *Aloe vera* leaves. The general methods of extracting pectins have been reported. See, Voragen et al, In *Food polysaccharides and their applications*. pp 287-339. Marcel Dekker, Inc. New York, 1995. See also, U.S. Pat. No. 5,929,051, the entire content of which is hereby specifically incorporated by reference. The extraction of *Aloe* pectin was achieved with a chelating agent such as EDTA or under other conditions including hot water, hot diluted acid (HCl, pH 1.5-3), and cold diluted base (NaOH and $Na_2CO_3$; pH 10).

Following the initial extraction, the remaining fibers were removed by coarse and fine filtrations. The pectin was precipitated with ethanol. The pectin precipitates were further rinsed with ethanol solutions before being dried.

*Aloe* pectins obtained in this manner from either pulp or rind cell wall fibers were characterized with a molecular weight (>$1\times10^5$ Da), a low DM (<50%), and a Gal A content (>80%). Preferably, the molecular weight was >$1\times10^6$ Da, the DM was <10%, and the Gal A content was >90%.

The molecular weight of the pectins was determined by HPLC-based size exclusion chromatography with pullulan as the standard. DM was determined by a selective reduction method (Maness et al., *Analytical Biochemistry* 185, 346-352, 1990) and a HPLC-based method (Voragen et al., *Food Hydrocolloids*, 1, 65-70, 1986). Gal A content was determined by m-hydroxyldiphenyl method (Blumenkrantz, N. and Asboe-Hansen, G. *Analytical Biochemistry* 54, 484-489, 1973). The content of each of these three references is hereby incorporated by reference.

In-Situ Gelation of *Aloe* Pectin Solutions Administered by Injection In Vivo

*Aloe* pectin was first dissolved in sterile deionized water and then mixed with equal volume of 2× physiological saline (0.3 M NaCl). *Aloe* pectin could not be readily dissolved in salt solution. However, once dissolved in water, the pectin can be mixed with the salt solution to achieve the physiological ionic strength. The pectin solution in physiological saline obtained in this manner remained clear. The pectin solutions were free-flowing at room temperature and had a pH of 5.0-6.0 depending on the polymer concentrations. No adjustment of temperature or pH was performed unless otherwise indicated. The preparation was injected subcutaneously into lower abdominal regions of Swiss Webster mice (0.05 or 0.1 ml per site) in accordance with the animal use protocols. Mice were sacrificed at various times following injection and the gel formation was examined.

The swelling of the skin at the injection site did not disappear over time as in the case of the saline control. When the skin over the injection site was surgically incised, a piece of gel shaped like a ball or an oval was observed. The gel was clear, transparent, and firm. It could be readily separated from surrounding tissues. The gel was surgically excised along with skin, fixed in formalin, sectioned, stained with H&E, and examined under the microscope. The gel was only lightly stained but was clearly visible and surrounded by the dermal tissues. The same in-situ gelation was also observed in rats. The swelling at the injection site was not as evident in rats as in mice due to the thicker skin and hair coat. However, when skin at the injection site was surgically incised, the same in-situ gel was observed. With rats, one ml of *Aloe* pectin solution could be injected subcutaneously at the lower abdominal region and correspondingly much larger gel pieces were obtained.

The gel formation is pectin concentration-dependent. At a concentration of χ 0.25% (w/v), a solid firm gel was obtained. No gel formation was observed at α 0.1% (w/v). At concentrations between 0.1% and 0.25%, a soft gel was obtained.

The in-situ gel also formed when the pH of the *Aloe* pectin solution was adjusted to ~7.2 with dilute sodium hydroxide.

The in-situ gelling ability is dependent on the molecular weight of *Aloe* pectin. When an *Aloe* pectin with a much reduced molecular weight (~$3\times10^4$ Da) but the same DM and Gal A content was used, no in-situ gelation was observed when tested at 0.5% (w/v).

The in-situ gel also formed following injection through intraperitoneal and intramuscular routes although the gel formed did not appear to have as uniform a shape as that formed following subcutaneous injection.

EXAMPLE 2

In-situ Gelation Following Topical Application to a Wound Surface

*Aloe* pectin preparation (0.5%, w/v) in physiological saline was directly applied to fresh full-thickness excisional skin wounds on mice or rats. A 0.5% (w/v) CMC preparation in physiological saline and a commercial hydrogel wound dressing were used as a control. The wounds were made with a biopsy punch in accordance with animal use protocols. After 4 hrs, rats were sacrificed and wounds surgically removed. Wounds were fixed in formalin, sectioned, and stained with H&E. A layer of gel was clearly visually observable on the surface of wounds with the *Aloe* pectin preparation but not with CMC or the commercial hydrogel wound dressing.

EXAMPLE 3

Pectin In-Situ Gelation Mediated by Calcium Ions in Body Fluids, as Measured by a Gel Frontal Migration Assay Body fluids such as blood, lacrimal fluid, lung fluid and nasal secretions contain calcium ions (8.5-10.3 mEq/dl in blood, for example). Since *Aloe* pectin forms calcium gel, the role of calcium in the in-situ gelation of *Aloe* pectin was examined using an in vitro gelling assay with animal serum that simulates in-situ gel formation. This in vitro assay is described as a gel frontal migration assay. Animal serum was placed at the bottom of a glass tube and the *Aloe* pectin solution was layered on top of the serum (the pectin solution may also be placed at the bottom of the tube dependent on the density of the test solution in relation to the pectin solution). Tissue culture grade normal calf serum was used. Two ml of serum was placed at the bottom of a glass tube (0.8×11 cm) and 1 ml pectin solution (0.5-0.75%, w/v) was placed on top of it.

Gel formation was immediate at the contact line (interface of the solutions) and the gel phase or gel front gradually extended upward in the pectin solution over time. The gel formed in the upper pectin phase can be distinguished from the pectin solution by its increased turbidity when examined under a light source. Also, tilting the tube does not move the interface if a gel is formed. The thickness of the gel formed at the interface can be measured over time (such measurements are referred to as "gel length" hereinbelow).

However, if the body fluid such as serum was first dialyzed against saline or EDTA (a chelator for divalent cations) to remove free calcium from the solution, or EGTA (a specific chelator for calcium) was added to the serum to a final concentration of 10 mM, no gel formation was observed. This is evidence that indicates that the calcium ions present in body fluids is involved in pectin in-situ gelation.

The pectin gelation also occurred when tested in similar in-vivo experiments with heparinized whole mouse blood or plasma isolated therefrom.

EXAMPLE 4

Pectin In-Situ Gelation with Other Body Fluids

Besides serum or blood, there are many other types of calcium containing body fluids such as tear fluid, lung fluid, and nasal fluid. To determine if the pectin gelation also occurred in in-vitro experiments with other body fluids, the gel frontal migration assay described in Example 3 was used along with Aloe pectin (0.25% in saline).

The gel formation occurred with natural peritoneal fluid. In this case, the ascites from mice injected with hybridoma for monoclonal antibody production was used as peritoneal fluid.

Gel formation also occurred with simulated body fluids such as:
1. Tear fluid (0.68 g NaCl, 0.22 g $NaHCO_3$, 0.008 g $CaCl_2.2H_2O$, and 0.14 g KCl per 100 ml. (See, Stjernschantz and Asitin, in Edman, P. (ed.), "Biopharmaceutics of Ocular Drug Delivery," CRC Press, Boca Raton, pp. 1-15, 1993. Alternatively, 0.268 g bovine serum albumin, 0.268 g lysozyme, 0.134 g globulin, 0.008 g $CaCl_2.2H_2O$, 0.650 g D-glucose, and 0.658 g NaCl per 100 ml. See, Cohen et al., *Journal of Controlled Release* 44, 201-208, 1997);
2. Lung fluid (0.01 g $MgCl_2.6H_2O$, 0.61 g NaCl, 0.03 g KCl, 0.027 g $Na_2HPO_4.7H_2O$, 0.007 g $Na_2SO_4$, 0.018 g $CaCl_2.2H_2O$, 0.095 g $NaHC_2O_2.3H_2O$, 0.26 g $NaHCO_3$, and 0.01 g $Na_3H_5C_6O_7.2H_2O$ per 100 ml. See, Fisher and Briant, *Radiation Protection Dosimetry,* 53, 263-267, 1994); and
3. Nasal secretion (0.867 g NaCl, 0.44 g $Na_2HPO_4$, 0.108 g $NaH_2PO_4$, 0.058 g $CaCl_2.2H_2O$, 0.31 g KCl 0.636 g albumin per 100 ml. See, Lorin et al., *Journal of Laboratory Clinical Medicine,* 2, 275-267, 1994).

EXAMPLE 5

NaCl Enhances Pectin Calcium Gelation

Body fluids such as blood and lacrimal fluids also contain sodium ions (135-146 mEq/L in blood). NaCl has been shown to enhance the calcium gelation of LM pectins. Pharmacological preparations for topical or parenteral use are commonly prepared in a buffered or non-buffered physiological saline (0.15 M NaCl) or isotonic solution. To determine if the enhancement of gelation induced by NaCl solutions also occurs with Aloe pectin, the gel frontal migration assay was used. Aloe pectin (0.5%, w/v) solutions prepared in 0.15 M NaCl (2 ml) were placed at the bottom of the tube and a less dense 100 mM $CaCl_2$ solution (0.05 ml) was placed on top of the pectin solution. The gel formed, extending downward in the pectin solution over time. The migration of the gel front downward into the pectin solution was measured at intervals following the addition of $CaCl_2$. The results showed that the gel front migrated faster in the presence of NaCl, i.e., the calcium gelation of Aloe pectin was enhanced by the presence of NaCl (See FIG. 1). The effect of NaCl was also calcium concentration dose-dependent; as the gel migration rate was faster in 0.15 M NaCl than in 0.05 M NaCl.

These observations are consistent with previous findings with other LM pectins (Garnier et al., *Carbohydrate Research* 240, 219-232, 1993; 256, 71-81, 1994).

FIG. 1 is a bar graph representing the relationship of NaCl to the calcium gelation of Aloe pectin.

EXAMPLE 6

Pectin In-Situ Gelation is Faster at Low Pectin Concentrations

Figure 2:
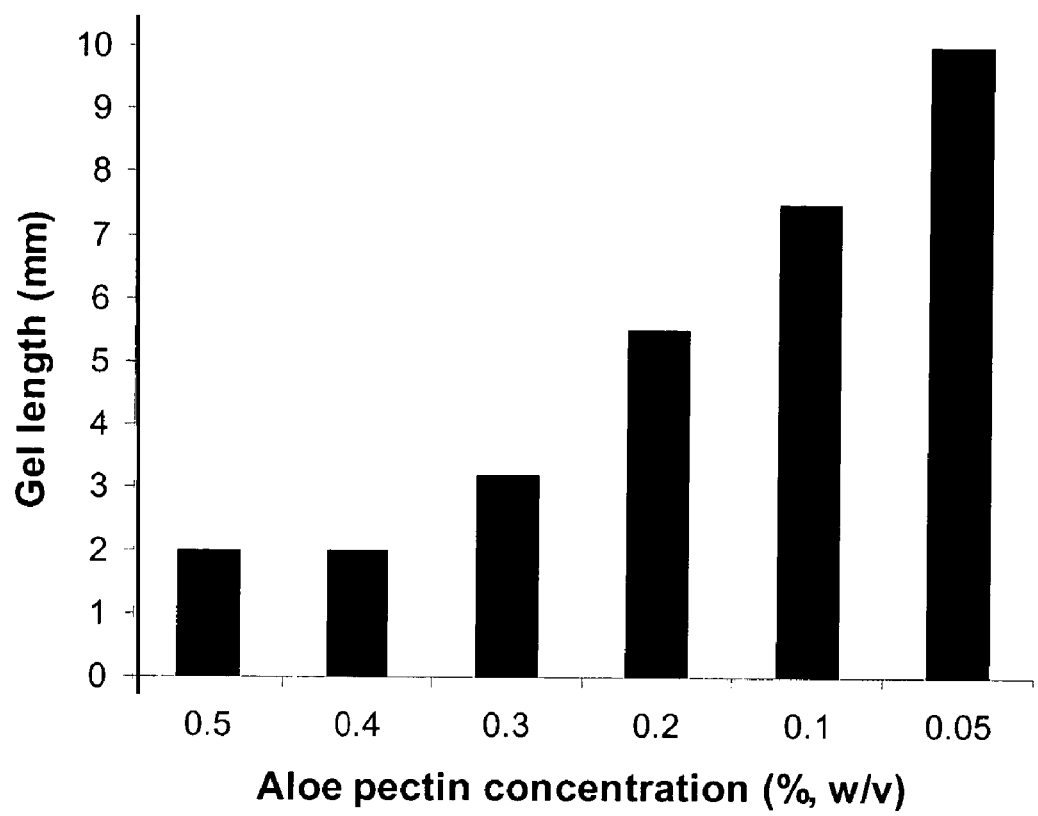
FIG. 2 shows the *Aloe* pectin in-situ gelation at various *Aloe* pectin concentrations with normal animal serum.

The gel frontal migration assay described above was used. Aloe pectin at various concentrations in saline (1 ml) was applied onto the normal calf serum (2 ml). After 18 hrs at room temperature, the length of gels formed (i.e. gel thickness) was measured. The initial gelation at the contact phase is immediate regardless of the pectin concentration. However, the rate at which the gel length grew over time differed at different pectin concentrations. It was found that the lower the pectin concentration, the faster the gelation; as the length of the gel formed at 0.05% (w/v) was nearly 5 times longer than that at 0.5% (w/v) (See FIG. 2). The gel formed at low concentrations (<0.2%, w/v) was much softer and could be broken by strong agitation.

The same observation was also made when a calcium chloride solution was used to replace the serum. This indicates that the rate of pectin calcium gelation is higher at lower pectin concentrations.

EXAMPLE 7

Figure 3:
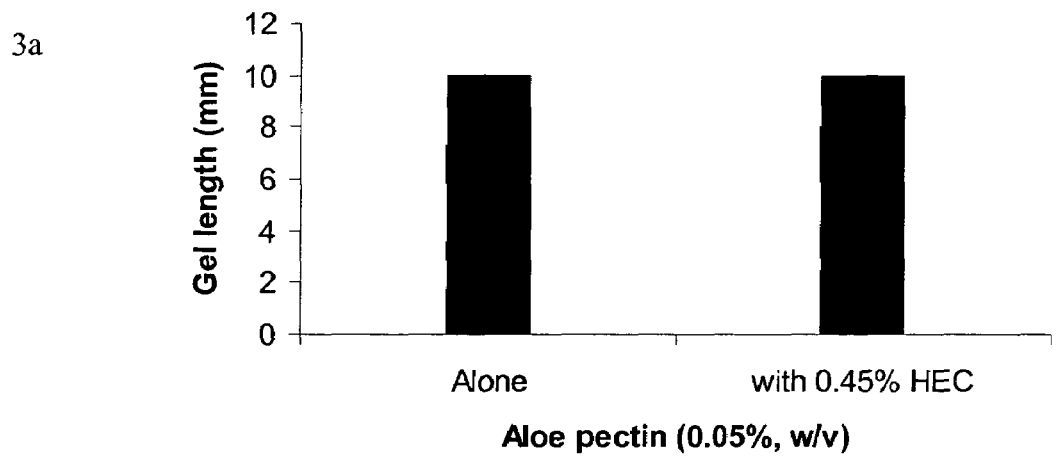
FIG. 3A shows the *Aloe* pectin in-situ gelation in the presence of a HEC thickener with normal animal serum.
FIG. 3B shows the *Aloe* pectin in-situ gelation in the presence of a sodium alginate thickener with normal animal serum.
Figure 3:
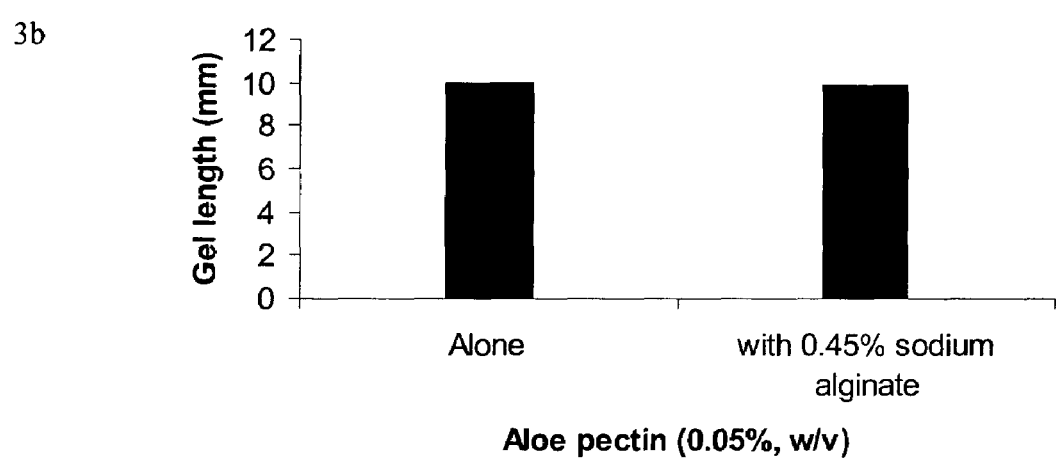

Addition of Other Polymers or Thickeners Enhances the Pectin In-Situ Gel Formation The gel frontal migration assay described above was used. Polymers such as hydroxyethylcellulose (HEC, 0.45%, w/v), carboxymethylcellulose (CMC, 0.45%, w/v), or sodium alginate (0.45%, w/v) were mixed with Aloe pectin (0.05%, w/v). Sodium alginate, although capable forming calcium gel with $CaCl_2$ solutions under in vitro conditions, did not form an in-situ gel with the serum. One ml of the polymer solutions were applied onto 2 ml normal calf serum in a gel frontal migration assay. The length of gels formed was measured 18 hrs later. The results showed that addition of other polymers did not influence the rate of the pectin in-situ gelation (See FIGS. 3A and 3B). The same result was also obtained when the polymer was mixed with Aloe pectin at a different ratio (0.4% vs 0.1%).

In an in vivo mouse experiment similar to those described in Example 1, a mixture of Aloe pectin (0.375%, w/v) and CMC (0.375%, w/v) in saline formed an in-situ gel following subcutaneous injection to the mouse. In addition, the addition of a thickener (sodium alginate or HEC at 0.4% or 0.3%, w/v) resulted in a better formed in-situ gel at lower Aloe pectin concentrations (0.1% or 0.2%, w/v) in which the in-situ gels were either soft or not formed with Aloe pectin alone (Example 1).

EXAMPLE 8

Comparison with Other Pectins and Alginates

Several polysaccharides other than Aloe Pectin that are capable of calcium gelation were used in in-vivo gelation experiments. The other polysaccharides included an LM pectin from citrus with a DM of 28% and a polygalacturonic acid prepared from apple pectin (DM=0), both of which were obtained from Sigma Chemical Co., and an amidated pectin with a DM of 28-34% and a DA (degree of amidation) of 16-22%. Before use, they were dissolved in de-ionized water, filtered, ethanol precipitated, and dried.

In-situ gelation experiments injecting mice with the solutions of the other pectins by subcutaneous route was performed as described in Example 1. Four injection sites on two mice were used for each sample. The results showed that following subcutaneous injection, no in-situ gel formation was clearly observed with any of the alternative polysaccharides at a concentration of 1.0 or 1.65% (w/v), as only smear-like gel substances were observed. However, when tested at a higher concentration (3.0 or 3.3%, w/v), well formed gels were obtained with both polygalacturonic acid and amidated LM pectin.

Similarly, the low molecular weight of *Aloe* pectin described in Example 1 also gelled in situ at a high concentration (2.5%, w/v).

An HM citrus pectin with a DM of 64% was also tested. It was prepared in the same way as that for the LM pectins. No gel formation was observed for the HM pectin at a concentration of 3% (w/v). The injection site was wet and watery and no solid gel pieces were observed.

Alginates were also tested, including Keltone HVCR and the high G alginate Manugel DMB (G content, 60-70%) at a concentration of 0.5%. Only a smear-like gel substance was observed when examined 4 hrs post subcutaneous injection, indicating that most of the materials had diffused away without gelling. The alginates also did not form a gel with the normal animal serum in the in vitro in-situ gelation assay as described above (Example 7). These results together showed that the LM pectin, polygalacturonic acid, amidated LM pectin, and alginate are much less efficient than *Aloe* pectin for in-situ gelation, under the same concentrations.

EXAMPLE 9

Delivery of Physiologically Active Agents by Pectin In-Situ Gel

For the in-situ gelation to be used for drug delivery, the phenomena must occur in the presence of the drug or diagnostic agents. Thus, various compounds or agents were mixed with *Aloe* pectin in physiological saline with a final pectin concentration of 0.5% (w/v). The experimental agents included a small molecule organic compound (fast green, N-Ethyl-N-(4-[(4-{ethyl [(3-sulfophenyl)methyl] amino}phenyl)-(4-hydroxy-2-sulfophenyl)methylene]-2,5-cyclohexadien-1-ylidene)-3-sulfobenzenemethanaminium hydroxide inner salt, disodium salt, 808 Da, 10 mg/ml), a small protein (bFGF, 17 kDa, 10 μg/ml), a medium-sized protein (bovine serum albumin, 66 kDa, 10 mg/ml), a large-size protein (type I bovine collagen, 2 mg/ml), a nucleic acid (Lamda DNA Hind III fragments, 200 μg/ml), a carbohydrate polymer (CMC, 0.5%, w/v), and Raw 264.7 cells (a mouse macrophage line, $1 \times 10^8$/ml). The mixtures were injected subcutaneously into mice. Gel formation was then examined 4 hrs after injection. The results showed that the in-situ gel formation occurred in the presence of all the agents occurred similarly to the gels formed with the *Aloe* pectin alone controls.

Furthermore, by gel frontal migration assay, the in-situ gelation of a 0.5% (w/v) *Aloe* pectin solution also occurred in the presence of 1) 0.1% (w/v) silvadene (silver sufadiazine), a poorly soluble anti-bacteria agent commonly used for wound treatment, 2) 0.5% (w/v) hydroxyethyl cellulose (HEC), and 3) 0.5% (w/v) sodium alginate (Keltone HVCR, Kelco). The presence of 0.5% (w/v) HEC or sodium alginate did not influence the efficiency of the in-situ gelation as described in Example 6.

Thus, the fact that the in-situ gelation occurred with these many different agents clearly indicates that the pectin in-situ gel can be used for delivery of a wide range of drug agents.

EXAMPLE 10

Figure 4:
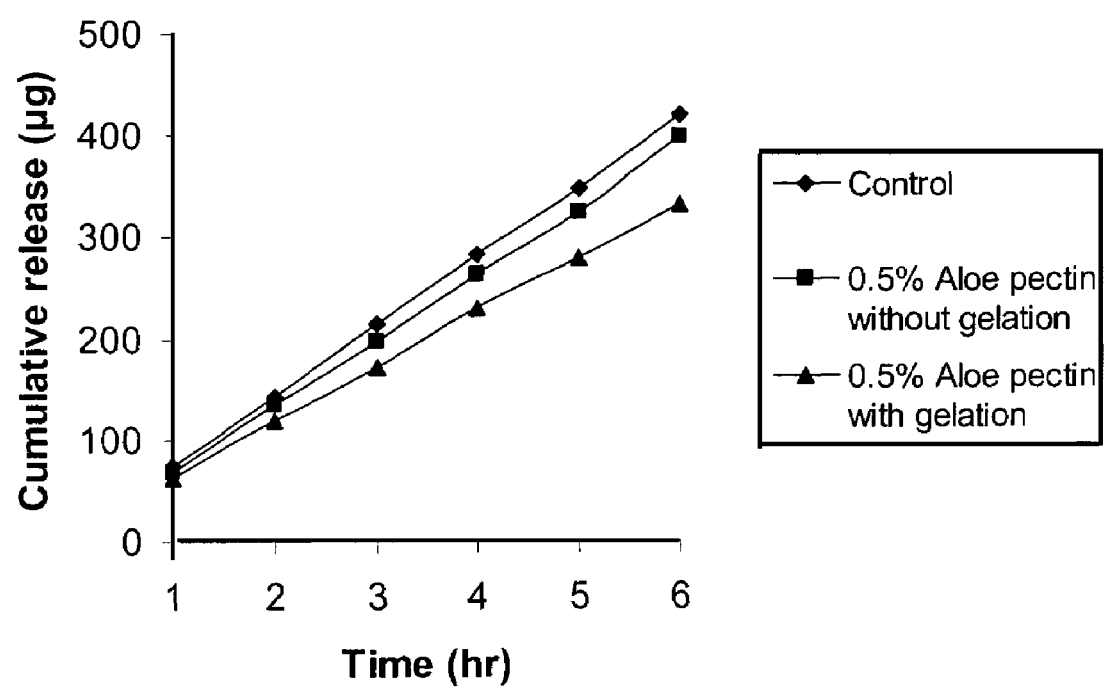
FIG. 4 shows the slow release effect obtained with *Aloe* pectin in-situ gel using a small organic compound (fast green).

Slow Release of a Small Organic Compound from Pectin In-Situ Gels Under In Vitro Condition Therapeutic and diagnostic agents vary greatly in molecular weight, from ~100 Da to over 10,000 Da. Generally, the smaller the compound, the more difficult to achieve a slow release effect. Here the small organic compound fast green, a dye which is widely used in the food and pharmaceutical industry, was chosen as a test compound. The dye was mixed with *Aloe* pectin (0.5%, w/v) in saline at a fast green concentration of 1 mg/ml. A pectin-free 1 mg/ml dye solution in saline only was used as a control. One ml of the dye/pectin preparation or the control was placed into a dialysis tube (1 cm in diameter) with a 12 kDa cut-off. Dialysis tubes with samples were then placed into 25 ml normal calf serum in 30-ml glass tubes. One serum tube receiving the dye/*Aloe* pectin solution also received EDTA to a final concentration of 10 mM to prevent calcium gelation. The serum tubes containing the samples were then shaken continuously at 100 rpm on a rotatory shaker. A small amount of serum (100 μl) was sampled at various time points. The amount of dye released into the serum was determined by measuring the OD at 620 nm. Serum samples with known amounts of fast green were used to establish the standard curve. The results showed that similar amounts of fast green were released from the control and dye/*Aloe* pectin with EDTA (without gel formation) and the amount of the dye released from the dye/*Aloe* pectin without EDTA (with gel formation) was significantly lower ($p<0.05$; student t-test) at the time points measured (See FIG. 4). This indicates that the presence of *Aloe* pectin and its gelation significantly slowed the release of the model small molecule pharmaceutical agent.

EXAMPLE 11

Slow Release of a Small Organic Compound from Pectin In-Situ Gels Following Subcutaneous Injection To determine if the above observed slow release could be obtained under in vivo conditions, the fast green (1 mg/ml)/ *Aloe* pectin (0.5%, w/v) in physiological saline or fast green in physiological saline alone was injected subcutaneously into mice. The injection sites (two per sample) were examined 4 hrs later. It was found that with the presence of pectin, in-situ gels were formed which partially retained the dye although the color was not as strong as the original preparation prior to injection. In contrast, the injection sites of the control had no gel and no color, and thus no retained dye.

Therefore, the pectin in-situ gel retained the dye and indeed slowed the release under the in vivo condition.

EXAMPLE 12

Local Delivery of bFGF by *Aloe* Pectin In-Situ Gel

Figure 5:
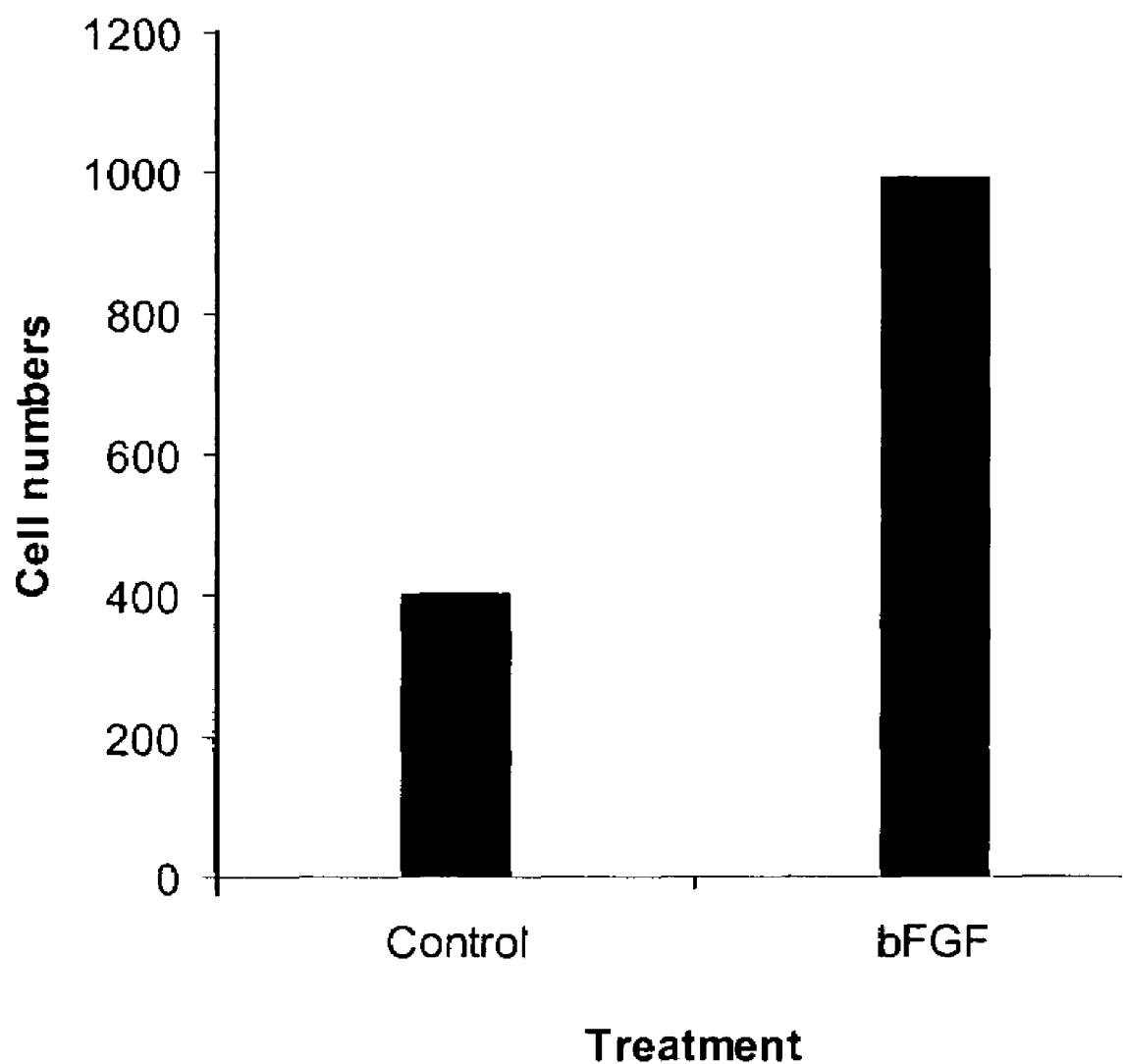
FIG. 5 shows a bar graph representing the relationship between bFGF treatment and cell number in a defined area.

For growth factors to exert local effect on tissues surrounding the administration site, they need to be delivered in a matrix to allow them to be released in a slow or sustained manner. A delivery in saline or buffer alone is not effective in this regard. In this example, a growth factor (bFGF) was used. bFGF (basic fibroblast growth factor or FGF-2) is a growth factor known to stimulate fibroblast proliferation and angiogenesis or blood vessel formation. It was mixed with *Aloe* pectin (0.5%, w/v) in physiological saline at a concentration of 1-10 µg/ml and then injected subcutaneously into the lower left or right side of abdominal region of mice. One side received the control (pectin alone), and the other side received the bFGF-containing preparation. The in-situ gels from two mice were harvested along with skin at days 5-10 and subjected to fixation in formalin, sectioning, and H&E staining. Two identical areas, at either end of the gel, vertically between the gel surface and the skin muscle layer and horizontally 510 µm inward from the lateral end of the gel were selected, and the cells in these two selected areas from each gel were numerated using the NIH image software. The results showed that the cell number was more than 2 times higher in bFGF-treated than the control (FIG. 5). An increase in blood vessel formation surrounding the gel was also observed at a high bFGF concentration (10 µg/ml). This indicates that bFGF was released from the in-situ gel and exerted its function in the surrounding tissues.

EXAMPLE 13

In-Situ Gelation of a Dried Pectin Composition

A mixture of an *Aloe* pectin and CMC (0.75% by weight each) and 1.5% CMC prepared in water were lyophilized in weighing trays, separately. The dried materials were cut out as round pads (about 1 cm in diameter and about 3 mm in thickness) and were immersed in a 10 ml of normal calf serum in a petri dish. The *Aloe* pectin/CMC pad formed a clear gel which remained intact for four days until the experiments were terminated, whereas pads containing CMC alone were dissolved or disappeared in a few hours under the same conditions. Thus, these results show that pectin in a dried form can also form a gel after being immersed in a body fluid.

EXAMPLE 14

Use of Pectin In-Situ Gel for Drug Delivery: Formulation Process

The pectin in-situ gel can be used to provide a physiologically acceptable composition that contains a therapeutic or diagnostic agent and a low concentration of a gelling polymer (pectin) with a pH and osmotic pressure characteristic of the body fluids, and that has the capability to change from liquid to gel upon administration.

The process to prepare a liquid formulation includes the following steps.
1. Pectin is dissolved in sterile water.
2. A buffered or non-buffered saline is prepared.
3. The two solutions are mixed.
4. A physiologically active compound is added to the preparation at step 3. The physiologically active agent may alternatively be added to either solution before mixing.

Besides water and buffered or non-buffered saline or aqueous solution, other pharmaceutically acceptable carriers may also be used, including emulsions such as an oil/water emulsion, adjuvant, various types of wetting agents, tablets, and capsules.

The pH of the formulation is adjusted with suitable buffering agents such as boric acid-sodium borate, sodium phosphate (monobasic)-sodium phosphate (dibasic), and Tris-HCl. Osmotic pressure of the formulation is adjusted to mimic that of body fluids with salts such as NaCl, KCL and $MgCl_2$, and other osmotic adjusting agents such as sorbitol, sucrose, glycerin, and mannitol.

A pharmaceutically acceptable thickener may be added. The thickener can be polyvinylpyrrolidone ("PVP"), modified cellulose polymers such as carboxymethylcellulose ("CMC"), hydroxymethylcellulose ("HPMC"), hydroxyethylcellulose ("HEC"), alginate, gelatin, dextran, cyclodextrin, or hyaluronic acid.

The formulation may be stored at room temperature or refrigerated (4° C.). If the formulation contains ~0.15 M NaCl, a (sodium) gel is formed when it is stored at 4° C. Prior to application, the gel is allowed to revert back to solution at room temperature. For drug or therapeutic agents that are particulate, prone to aggregate formation, or have a low water solubility such as silvadene (silver sulfadiazine), storage in a gel matrix may be advantageous because it may prevent aggregate or precipitate formation.

Alternatively, the formulation may be prepared in a dried form. A mixture of a pectin and a physiologically active agent in buffered or non-buffered water or saline are lyophilized. Alternatively, a pectin powder and a dry physiologically active agent are blended and compressed into a desired form. The dried form may be used as a pad, a tablet, a capsule, or a powder.

The relative amounts of the physiologically active agent and the pectic substance in the formulation or composition can vary widely dependent on the particular agent to be delivered. In a liquid formulation, the agent can range from about 0.01% to about 50% (w/v) while the pectic substance can range from about 0.01% to about 40% (w/v). In a dried or suspended formulation, either the agent or the pectic substance can range up to over 90% (w/w).

EXAMPLE 15

Preparation of Pharmaceutical Powder Formulations Comprising Assorted Anionic Polysaccharides, and their Gel-Forming Properties Powder formulations comprising model active agents, various anionic polysaccharides, thickeners, and an optional excipients, as detailed below in Table 2 were prepared. The ionic polymers used to prepare the formulation are listed below.

High Molecular Weight *Aloe* pectin, (HMW AP), DM<10%, Mw>$1.0 \times 10^6$ Da

Low Molecular Weight *Aloe* pectin (LMW AP) DM<10%, Mw=$1.3 \times 10^5$ Da

Polygalacturonic acid, (Poly Gal A) from Sigma, DM<3%, Mw=$1.7 \times 10^5$ Da

Low Molecular Weight Pectin (LM Pectin) DM=26%, Sigma, Mw=$2.0 \times 10^5$ Da

Alginate, medium viscosity, Sigma Chemical Co.

Molecular weights were determined by Size Exclusion Chromatography using pullulan as a standard via the procedure described in example 10 of U.S. Pat. No. 5,929,051. SEC was performed using TSK-Gel G5000 PWX column (Toso Haas). Samples were prepared at 0.3 mg/ml in water with 0.05% (w/v) sodium azide. 50 µl of the sample was injected and eluted with 0.05% sodium azide at 1 ml/min. Refractive index was measured in line. Pullulans ($4.04 \times 10^5$, $7.88 \times 10^5$, and $1.66 \times 10^6$ Da) were used as standards. The molecular weight was calculated against the linear regression line of the standards.

The now commercially available *Aloe* pectins are highly purified and micro-filtered and are made under cGMP (current Good Manufacturing Practice). The other polysaccharides listed in the table above all contained a considerable amount of insoluble material and produced cloudy solutions when dissolved in water. They were all micro-filtered to remove insoluble materials, precipitated with alcohol, and dried before use. Bovine serum albumin (BSA) and lysozyme were initially used as pharmaceutically active agent. BSA is widely used for examining various pharmaceutical formulations as a model agent, especially those for protein delivery. Lysozyme is known to be antibacterial. Povidone (polyvinylpyrrolidone, K29-32) was used as a thickener and lactose was used as a excipients, and both were obtained from Sigma Chemical Co.

Powders formulations were made by preparing a liquid mixture of all the ingredients listed in Table 2 and then lyophylizing the solution, to form a lyophilized solid. The compositions of both the liquid precursor solutions and the final powders are shown in Table 2.

TABLE 2

Sample Compositions
liquid (%, w/v) and dried (%, w/w)*

| | #1 | #2 | #3 | #4 | #5 |
|---|---|---|---|---|---|
| Polymer | HMW AP | LMW AP | LM pectin | PolyGal A | Alginate |
| | 0.4 | 0.8 | 0.8 | 0.8 | 0.8 |
| | (0.03) | (0.06) | (0.06) | (0.06) | (0.06) |
| Povidone | 7.5 | 7.5 | 7.5 | 7.5 | 7.5 |
| | (57.69) | (56.39) | (56.39) | (56.39) | (56.39) |
| Lactose | 5 | 5 | 5 | 5 | 5 |
| | (38.46) | (37.59) | (37.59) | (37.59) | (37.59) |
| Active agent | 0.1 | 0.1 | 0.1 | 0.1 | 0.1 |
| (BSA or lysozyme) | (0.0077) | (0.075) | (0.075) | (0.075) | (0.075) |

*Numbers in parenthesis indicate the percent content of each ingredient in dried form on the moisture-free basis (w/w).

The lypholized solids were milled using an Eberbach blender with a micro-container. The resulting powder was sieved using a sterile 100 µm nylon membrane sieve to produce powders with a particle size <100 µm and then sequentially with sterile nylon membranes of various pore sizes (40, 70, and 100 µm; Cell strainer, Becton Dickinson Labware), yielding powders of various particle sizes (<40, 40-70, and 70-100 µm). The >100 µm particles were also further sieved using a 200 µm sieve to produce 100-200 µm particles. The sieving was performed under vacuum using a glass filter holder and the powders were collected onto a 0.22 µm membrane. The powders were stored at room temperature.

Control powders were also made with formulations having all components, except for the ionic polymers.

Two powder formulations made with HMW *Aloe* pectin according to Table 2, one sample with BSA and another control without BSA, were prepared, milled, and sieved to <100 µm. The moisture content of both these two samples was determined to be 2-3% (w/w) using a moisture analyzer at a drying temperature of 120° C.

EXAMPLE 16

Gelation Properties of Powder Formulations

To demonstrate gel formation properties of the powder formulations whose preparation is detailed in Example 15, powders (10 mg, <100 µm) made with the various pectins and alginate were suspended in 2 ml saline solutions. The saline solutions of one sample set comprised 3 mM calcium chloride, and the other did not comprise calcium chloride. In the presence of calcium, the powder particles hydrated but remained in the form of particles, and the suspension remained cloudy. Under the microscope, the powder particles in calcium saline changed into clear and transparent gel particles or pieces. In contrast, in the absence of the calcium the particles quickly dissolved within ~10 min and the suspension changed into a clear solution (except for the powder made with the high molecular weight *Aloe* pectin, which is not readily soluble in typical NaCl saline but also does not gel in the saline, see discussion below).

When the calcium chelating agent EDTA (10 mM) was added to the powders suspended in calcium saline describe above, the particles quickly dissolved within ~10 min.

Similar results were obtained when the powders made with pectins or alginate were suspended in normal calf serum. That is, powder particles remained in the form of solid particles after being suspended in calcium containing normal calf serum. But, upon addition of EDTA the particles mostly dissolved in ~10 minutes. Similar results were also obtained in simulated nasal fluid (0.867 g NaCl, 0.44 g $Na_2HPO_4$, 0.108 g $NaH_2PO_4$, 0.058 g $CaCl_2.2H_2O$, 0.31 g KCl per 100 ml. See, Lorin et al., *Journal of Laboratory Clinical Medicine*, 2, 275-267, 1994). These experiments are evidence that the powder particles suspended in the solutions containing free calcium ions formed a calcium crosslinked gel, but in the absence of calcium, or if the calcium was removed from the gel by the chelating agent, no gel was formed or was stable, and the polysaccharide particles dissolve.

As noted above, HMW *Aloe* pectin is soluble in water, but is not readily soluble or only partially soluble in NaCl saline or buffered saline. Powder particles comprising HMW *Aloe* pectin recovered from NaCl saline solutions by centrifugation (500 g for 5 min) and re-suspended in water quickly dissolved in a few minutes. This behavior contrasts with particle made from low molecular weight LM pectins, polygalacturonic acid, LMW *Aloe* pectin, or alginate, which are readily soluble in both water and NaCl saline solutions. Nevertheless, particles prepared from particles isolated from calcium-containing saline or normal calf serum solution remained in the form of particles when placed in water, indicating the various polysaccharide powder particles had all gelled in the presence of calcium ions.

EXAMPLE 17

Comparison of Solid and Liquid Formulation for Gel Formation and Control of Drug Release Liquid formulations consisting of aqueous solutions of different anionic polysachharides and Fast Green dye (1 mg/ml) were prepared. Fast Green was used to simulate a small molecule therapeutic agent. The concentrations of anionic polysaccharide polymers employed were 0.5% for HMW *Aloe* pectin, 1% for alginate, and 2% for polygalacturonic acid, LMW *Aloe* pectin, and LM citrus pectin. To prepare the solid formulations, 20 microliters of the aqueous formulations were placed on a weighing tray as a drop, lyophilized, and then recovered as a dried disc.

The dried formulation discs, or 20 microliters of the liquid formulations, were placed in 3.5 mililiters of normal calf serum in 60 mm petri dishes, with or without the addition of 10 mM EDTA. The diffusion of the Fast Green dye, which simulates the release of a drug agent, was observed by measuring over time the diameter of green dye diffusion circle around the initial insertion points of the formulations.

In normal calf serum without EDTA, the dried formulation discs remained in the form of a solid disc and gradually changed into clear and solid gel pieces. After 24 hours, when all the dye diffused away, the gels from the dried formulation tuned clear and transparent. The gel formation of the dried formulation was further confirmed by soaking the gel discs in saline with 10 mM EDTA, wherein it quickly dissolved in ~30 min. In normal calf serum containing EDTA, the dried formulation discs also gradually dissolved, as either a disc or film.

In contrast, most of the liquid formulations gradually dissolved and/or diffused away, without formation of distinct gel pieces resembling the original drop, and formed only a thin layer of gel pieces as detected after gently shaking the petri dishes after 2 hours. Therefore it appears that the powder formulations gelled more effectively than the liquids. Nevertheless, when dropped into a 50 mM $CaCl_2$ solution though a 25 G needle, the liquid formulations all held together and formed gel beads. Nevertheless, liquid formulations made with HMW *Aloe* Pectin held together and formed a small piece of gel with a size only slightly bigger than the original drop size in the serum. This underscores the high efficiency for gel formation shown by the high molecular weight *aloe* pectins. Together, these observations indicate that the efficiency of in-situ gel formation of a dried formulation can be superior to that of a liquid formulation.

Figure 6:
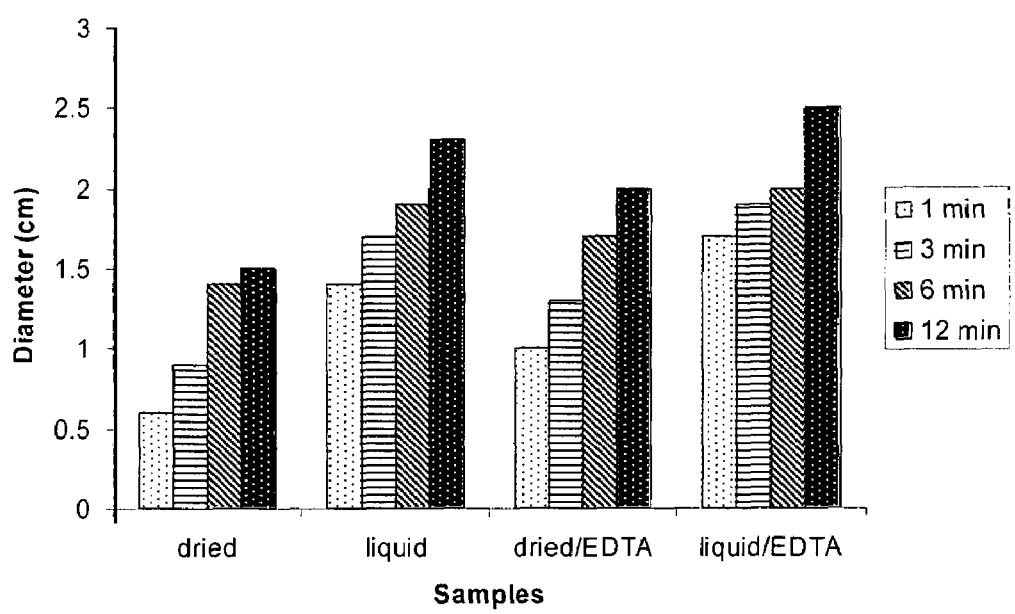
FIG. 6. The release rate of fast green from liquid or dried formulations.
Figure 6:
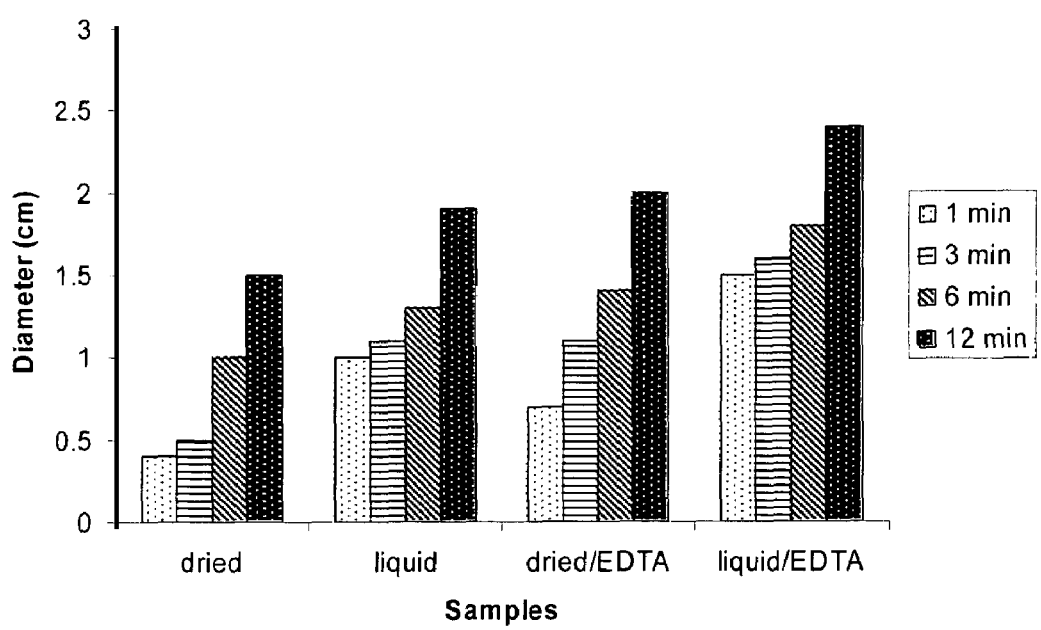

The diameters of the diffusing Fast Green circle around the formulations immersed in normal calf serum with and without EDTA were measured over time with both dried and liquid formulations (see FIG. 6). It appear that the gel formation in either solid or liquid samples without EDTA slows the dye or drug release consistent with the observation that gel formation is more efficient with the dried formulation. The same observation was observed with all formulations, except for the dried formulation with HMW *Aloe* pectin which exhibited a dye diffusion that was only slightly faster in sera with EDTA than the one without EDTA. This may be related to that the fact that HMW *Aloe* pectin is less soluble or insoluble in saline, which again, is another distinct feature of the HMW *Aloe* pectin.

EXAMPLE 18

Use of Powders Comprising Soluble Calcium Salts to Induce In-Situ Gelation of Polysaccharide/Agent Powder Formulations Two powder formulations comprising a protein active agent (BSA) and a polysaccharide selected from LMW *Aloe* pectin or alginate (as described in Table 2, samples 2 and 5) were sieved to produce powders having particle sizes under 100 μm. A calcium-containing powder was made from a liquid formulation comprising 2.5% (w/v) polyvinylpyrrolidone, 10% (w/v) lactose, and 1% (w/v) calcium chloride, drying the solution, and grinding the solid and sieving the powder to particle sizes of <40 μm, produce a gel inducing powder with a calcium chloride content of 7.4% after drying.

The polysaccharide powders and gel inducing powders were mixed 4:1 by weight, resulting in a final calcium chloride content of the powder mixture of 1.48% (w/w).

The powder mixture was suspended in saline (5 mg in 1 ml). All three unmixed powders (i.e. pectin+protein, alginate+protein, and calcium-containing gel inducing powder dissolved when suspended individually in NaCl saline. Nevertheless, mixtures of the calcium gel inducing powder with powders comprising LMW *Aloe* pectin+protein, or alginate+protein did not dissolve in NaCl saline. The same results were also obtained with lysozyme as the active agent. These results suggest that the calcium containing powder induced the polysaccharide/protein powders to gel when in contact with a saline solution model of a body fluid.

EXAMPLE 19

Use of Powders Comprising Poorly Soluble Multi-Valent Cation Salts to Induce In-Situ Gellation of Polysaccharide/Agent Powder Formulations Aluminum hydroxide ($Al(OH)_3$) is poorly soluble in water, but has been approved as a pharmaceutical adjuvant for human use. An aluminum hydroxide suspension purchased from Sigma Chemical Co. was a whitish, cloudy, but homogenous particle suspension. An *Aloe* pectin solution (2 mg/ml in water) formed a gel when mixed with the insoluble aluminum hydroxide gel suspension, as indicated by the formation of visible large aggregates of aluminum hydroxide particles. The same observations were also observed with other pectins and alginate. The aggregates were large and easily visible when proper polymer/aluminum hydroxide ratio were reached. Similar results were also observed with calcium phosphate (Sigma Chemical Co.), although the aggregates formed were not as large as those with aluminum hydroxide. Both aluminum hydroxide and calcium phosphate are relatively insoluble materials (Merck Index, 13$^{th}$ ed.), but these poorly soluble salts apparently ionized at the surface when hydrated, allowing reaction with the *Aloe* pectin.

To further explore this observation, aluminum hydroxide and calcium phosphate powders were suspended in water or saline (10 mg/ml) and then mixed with HMW *Aloe* pectin solution at various final concentrations (2.5-0.0012 mg/ml). The same gel formation indicated by large aggregate formation was observed. The same observation was also made with alginate, LM pectin, and polygalacturonic acid, indicating that it is possible to use poorly soluble metal divalent or multivalent cation salts as a gel-inducing agent.

As an example, a powder formulation made with *Aloe* pectin (HMW) as in example was mixed with aluminum hydroxide powder at a 3:1 ratio. The mixtures (10 mg) were suspended in 2 ml saline. Large aggregates were immediately formed. Toluidine blue was added to the suspension to stain the ionic polymer powder particles. After 30 minutes or more, a small drop of the suspension was placed onto a glass slide and observed under a microscope. The aggregates consisted of both pink-stained formulation powder particle and the opaque grayish aluminum hydroxide particles, confirming the aggregate formation.

As a second example, a powder formulation made with LMW *Aloe* pectin was mixed with aluminum hydroxide powder at 3:1 ratio, and the powder mixture suspended in the saline. Although aggregates formed, there were few pink-stained formulation powder particles observed under the microscope and the aggregates appeared to consist primarily of the aluminum hydroxide particles. This indicates that the formulation powder particles dissolved and the insoluble salts did not cause gelation of the whole formulation particles.

However, when the polysaccharide formulation/aluminum hydroxide powder mixture was suspended in saline comprising 3 mM calcium chloride, the polysaccharide formulation particles were again observed, aggregates also formed consisting of the formulation particles and the aluminum hydroxide particles. The same aggregate formation was also observed when the mixture was suspended in normal calf serum.

The poorly soluble metal ion salts may not easily penetrate polysaccharide containing formulation particles, and therefore may not cause gellation of the whole particles, and may only cause the polymer cross-linking or gellation on the surface of the particles. Because they are only poorly soluble, or close to insoluble, the undissolved multi-valent cation-containing particles can act as a physical carrier for a gel, or as a long-lasting source of crosslinking divalent or multi-valent cations. Additionally, the formulation powder particles and the poorly soluble solid gel-inducing agents can cause the formation of gelled aggregate compositions. Dependent on the ratios and relative particle sizes of these two different powders in a mixture, the size and other characteristics of the aggregates formed can be varied and/or modulated. At a high or low ratio, the aggregate particles sizes can be very small, with one particle of one type surrounded by particles of another type, whereas at a ratio of ~1, the particles can interconnect as a network, forming a large network. Therefore, aggregate gel complexes formed under various conditions can be used to modulate the physical, solubility, and time release characteristics of in-situ gels formed at a site of administration, such as mucosal surfaces and/or the nasal cavity.

EXAMPLE 20

Sustained Release of Pharmaceutically Active Agent from Powder Formulations

The effect of in-situ gelling powder formulation on the release of the active agent was evaluated using simulated nasal fluid (SNF) as a release media. The powder formulations were made as above with various amounts of povidone and lactose, but all had same protein (BSA) content (0.1% on dry weight basis) (See Table 3). Control powders contained all components except for the ionic polymer (HMW Aloe pectin).

TABLE 3

| | Formulation Composition liquid (%, w/v) and dried (%, w/w)* | | | |
|---|---|---|---|---|
| | 1 | 1 Control | 2 | 2 Control |
| HMW AP | 0.4 | 0 | 0.4 | 0 |
| | (2.6) | (0) | (3.1) | (0) |
| Povidone | 15 | 15 | 2.5 | 2.5 |
| | (97.3) | (99.93) | (19.3) | (19.97) |
| Lactose | 0 | 0 | 10 | 10 |
| | (0) | (0) | (77.4) | (79.9) |
| BSA | 0.015 | 0.015 | 0.0125 | 0.0125 |
| | (0.097) | (0.099) | (0.097) | (0.099) |

*on the moisture-free basis.

Figure 7:
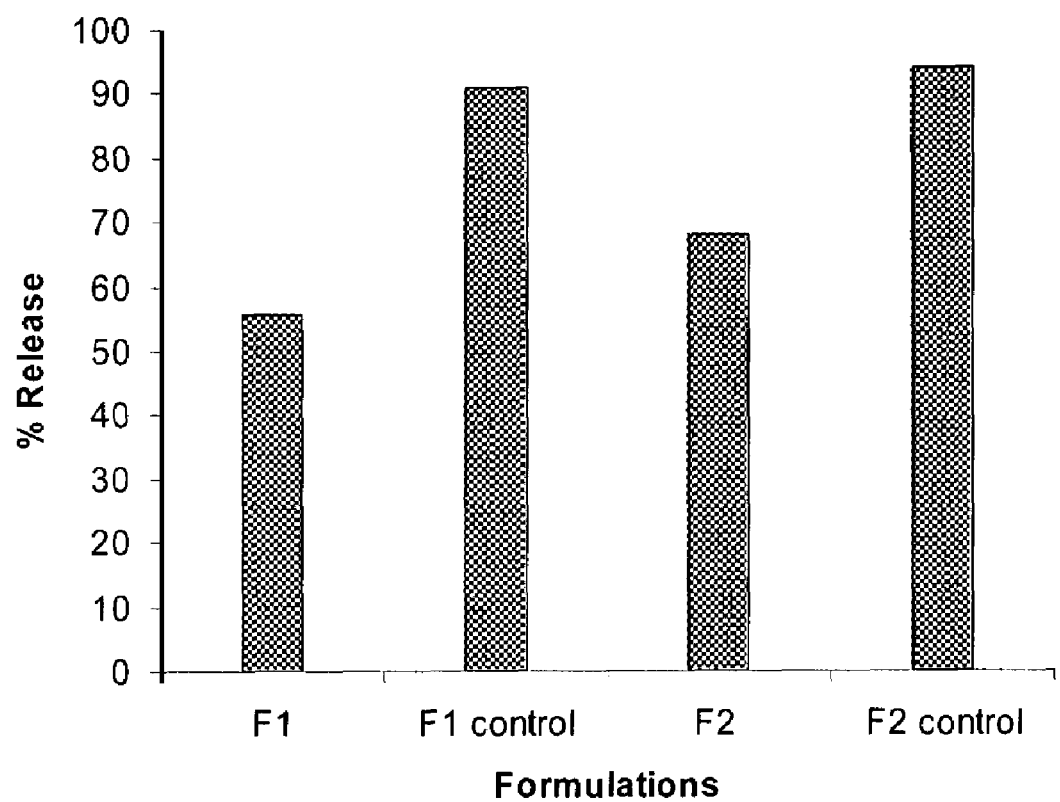
FIG. 7. Controlled protein release from powder formulations comprising a high molecular *aloe* pectin, and suspended in simulated nasal fluid, as described in Example 20.

Ten mg of powders were suspended in 0.25 ml SNF. After 30 min, the solution or supernatant was separated from the particles or pellet by centrifugation and the protein in the supernatant and pellet were analyzed by SDS gel electrophoresis and densitometry analysis. The percent release of the protein agent from each formulation was determined by the following formula—[protein in supernatant/(protein in supernatant+protein in pellet)]×100%. It was observed that proteins were almost all released from the control powders (>90% released), which were all completely dissolved. On the contrary, the protein release was significantly slowed from powders with Aloe pectin; only 55% (formulation 1) or 68% (formulation 2) was released with powders made with the ionic polymer (FIG. 7). Similar results were also obtained with lysozyme as the active agent. It was also found that protein release was faster from formulation 2 than formulation 1. The formulation 2 had 2.5% PVP and 10% lactose, whereas formulation 1 contained 15% PVP and no lactose (Table 3). This indicates that the release rate can be further adjusted by the amount and type of excipients used.

EXAMPLE 21

Physical Mixtures of Powders of Pharmacalogically Active Agents, Polysaccharides, Gel Inducing Compostions, and Other Excipients A powder formulation as in Table 2 is made in the absence of an active agent and sieved to an appropriate size. A powder of an active agent made with or without a pharmaceutically acceptable excipitent is then blended with the polymer powder. One or more solid gel inducing compositions as described elsewhere herein may also be optionally included. The mixture of powders is then delivered to an animal.

EXAMPLE 22

Intranasal Delivery of a Powder Vaccine Formulation Comprising an Antigen to an Animal A powder vaccine formulation comprising high molecular weight Aloe pectin and a diphtheria toxin mutant CRM (DT-CRM) antigen was prepared by dissolving the components listed in Table 4 in an aqueous solution, lyophilizing the solution to produce a powder, grinding the powder, then sieving the powder. Control formulations containing all the ingredients except for the antigen were similarly prepared.

TABLE 4

| Components | Antigen formulation liquid (%, w/v) and dried (%, w/w) | Control formulation liquid (%, w/v) and dried (%, w/w) |
|---|---|---|
| HMW AP | 0.4 | 0.4 |
| | (3.1) | (3.1) |
| Povidone | 2.5 | 2.5 |
| | (19.4) | (19.4) |
| Lactose | 10 | 10 |
| | (77.5) | (77.5) |
| DT-CRM | 0.01 | 0 |
| | (0.077) | (0) |

The vaccine formulations were made to deliver 7.75 µg antigen per 10 mg powder formulation. Rats weighing 200-250 grams were first anesthetized and 10 mg the powders were delivered into each nostril using a 200 µl pipette tip connected to a 5 ml syringe, using 3 ml of air through a rubbertube as previously described (Ryden and Edman, Int. J. Pharm. 83 (1992), pp. 1-10; Schipper et al., Pharm. Res. 10 (1993), pp. 682-686).

Serum samples were collected from the rats one week after inoculation and specific serum IgG (immunoglobulin G) was assayed via ELISA (enzyme-linked immunosorbent assay). The end point for IgG titer was determined as the reciprocal of the highest dilution that has an absorbance value 50% greater than the background (absorbance of the antigen-coated wells without serum added).

The two rats that received the DT powder developed specific antibodies to the DT-CRM antigen with a mean IgG titer of 800 after only one week. The two control rats that received the control formulation having no DT-CRM antigen develtogether, then the tubes were kept at room temperature and observed over time. A complete or partial gel formation clearly occurred upon mixing at a final calcium chloride concentration above 0.03125% (w/v) (2.125 mM) since the solution was completely or partially solidified and no longer free-flowing when tubes were tilted. At a concentration of 0.0156% $CaCl_2$ the viscosity of the solution was increased and granular gel pieces were present. However, at a final concentration of <0.0078% (0.53 mM) or lower, there was no hint of gel formation and the mixture remained homogenous and remained so after more than 24 hrs.

TABLE 5

|  | Concentrations (%, w/v, final)* | | | | | | | | | |
| --- | --- | --- | --- | --- | --- | --- | --- | --- | --- | --- |
|  | 0.5 | 0.25 | 0.125 | 0.0625 | 0.0313 | 0.0156 | 0.0078 | 0.0039 | 0.0019 | 0 |
| $CaCl_2 \cdot 2H_2O$ | + | + | + | + | + | ± | − | − | − | − |
| $ZnCl_2$ | + | + | + | + | + | ± | − | − | − | − |

Figure 8:
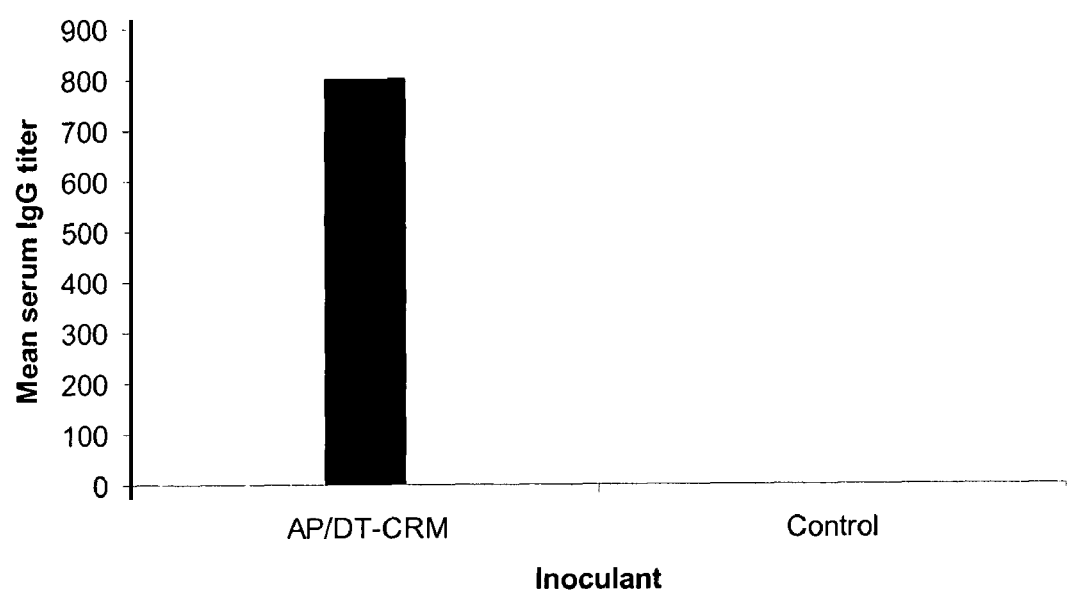
FIG. 8. Specific serum IgG response against DT-CRM antigen following intranasal delivery to rats of a powder vaccine formulation, as described in Example 22.

*+ indicates whole gel formation, ± partial gel formation, and − no gel formation and solution remains clear and homogenous.

oped no such antibodies (FIG. 8). This result indicates that nasally administering the powder vaccine formulation effectively induced a specific immune response in the rats.

EXAMPLE 23

Delivery of Powder Formulations to Animals Parenterally

As described in Example 16, powder particles remain as particles or change into gel particles when suspended in calcium-containing saline. Thus, the powders may be injected as a particle suspension after being suspended in a calcium saline or calcium buffered saline. Alternatively, the formulation powders may be pre-mixed with calcium powders as described in example 17 wherein the powders are suspended in saline or buffered saline prior to injection into the tissues of an animal. The formulation powders described in Example 16 having a powder particle size <100 µm were employed, although smaller powder particle sizes can be desirable for embodiments related to injection of suspended powders.

Each powder (80 mg) was suspended in 0.4 ml saline containing 3 mM $CaCl_2$ and injected subcutaneously into mice (0.1 ml per injection site, two sites/mouse). At 4 hours post injection, the mice were sacrificed, the skin peeled open, and the injection sites were examined. A small nodule or swelling area representing the hydrated and gelled particles was observed at an injection site with powder formulations with an ionic polymer. In contrast, no such small nodule or swelling area was observed with the control powder made without an ionic polymer. Additionally, the injection sites were very moist, including those from the control, perhaps because of the presence of polyvinylpyrrolidone, which is a highly water-absorbing polymer.

EXAMPLE 24

Figure 9:
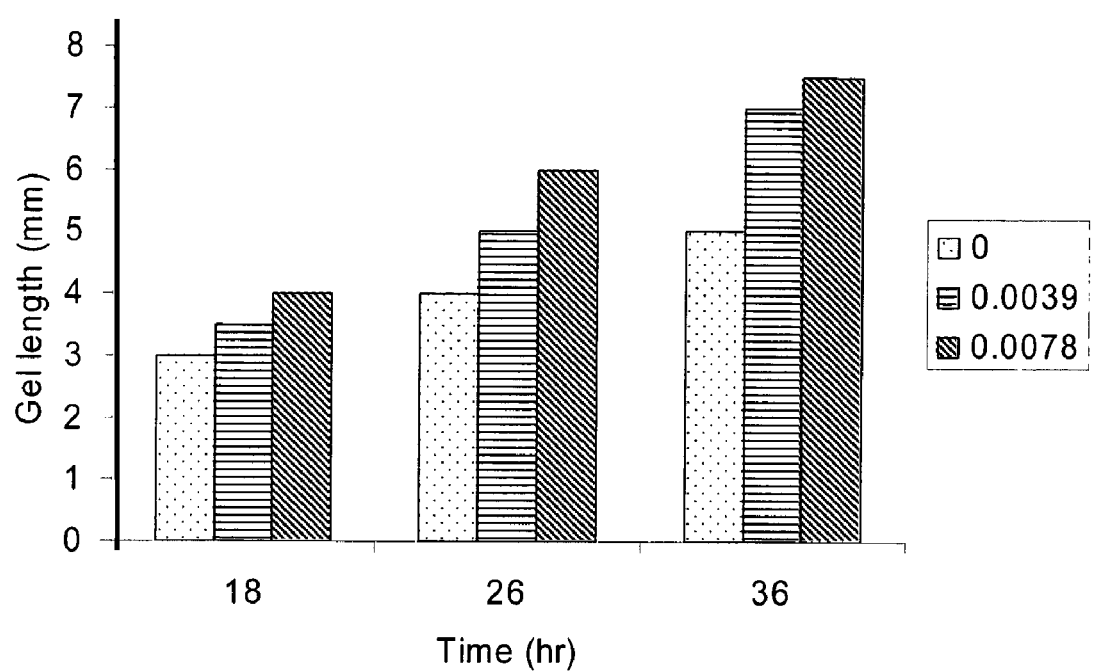
FIG. 9. Improved in-situ gelation of pectin formulations in contact with normal calf serum is achieved by addition of extraneous calcium, as described in Example 24.

Gelation of Liquid Formulations as Influenced by Exogenous Gel-Inducing Agents and Compositions A 0.6% (w/v) HMW *Aloe* pectin solution in water was mixed with calcium chloride dihydrate solutions at various concentrations, at an 1:1 ratio (1 ml to 1 ml) to achieve a final polymer concentration of 0.3% (w/v) and a final calcium chloride dihydrate concentration from 0.0019-0.5% (w/v). See Table 5 below. The mixtures were immediately vortexed To demonstrate that incorporation of the divalent cation can increase the in-situ gelation, a gel frontal migration assay with normal calf serum was performed as described in Example 3. Thus, 1 ml 3 mg/ml pectin solutions containing 0%, 0.0039%, or 0.0078% calcium chloride or zinc chloride was gently layered on to 3 ml normal calf serum in a 10×75 mm glass test tubes. Starting at the interphase, gel gradually formed in the pectin solution phase. The gel could be readily identified under a light source due to its slightly increased turbidity as compared to the solution. Thus, the length (thickness) of gel in the pectin solution phase at the interface was measured over time. The results showed that gel formation increased at both exogenous calcium chloride concentrations tested when compared to the control that has no added calcium chloride (FIG. 9).

It should be noted that the results in Table 5 can be advantageously employed, in that small amounts of a divalent cation such as calcium or zinc (i.e. below about 0.0156% (w/v) can be added to pectin/agent solution without causing significant gellation, with the unexpected result that when the solution is administered to a tissue or body fluid comprising calcium ions, improved gellation will be induced.

EXAMPLE 25

Effect of Various Monovalent Cations on the Solution Properties of LM Pectins

NaCl and $NH_4Cl$ were prepared in water at various concentrations. They were then mixed 1:1 v/v with solutions of LM pectin, HMW *Aloe* pectin, or a HM pectin. The HM pectin (DM=64%, Sigma chemical Co) was filtered to remove insoluble materials as described in Example 15. The solutions were then observed at room temperature for 1 hr. They were then cooled at 4° C. for 2 hrs or longer and examined again.

The pectins with a degree of methylation below 50% exhibited a salt concentration-dependent precipitation of pectins at room temperature (see Tables 6 and 7). HMW *Aloe* pectin was most prone to precipitate formation, followed by the LM pectin. Using HMW *Aloe* pectin, a pectin concentration-dependent effect was also observed, i.e., pectin at a lower concentration is less prone to precipitate formation. For example, precipitate formation slowly occurred in 0.15 NaCl with a 0.5% HMW *Aloe* pectin solution, but not with a 0.1% pectin solution. In addition, there was an effect of molecular weight, since no precipitation was observed with 0.5% LMW *Aloe* pectin in 0.15 M NaCl. HM pectin solutions did not form precipitate or gel with either salt at any concentration or temperature tested.

TABLE 6

|  | NaCl (M) | | | | | | | |
| --- | --- | --- | --- | --- | --- | --- | --- | --- |
|  | 0 | 0.1 | 0.15 | 0.2 | 0.4 | 0.6 | 0.8 | 1.0 |
| HMW AP (MW = 15 × 10$^5$) | | | | | | | | |
| 0.1% | —(—) | —(—) | —(G) | —(G) | P (P) | P (P) | P (P) | P (P) |
| 0.5% | —(—) | —(G/P) | P (G/P) | P (P) | P (P) | P (P) | P (P) | P (P) |
| LM pectin (0.5%) | —(—) | —(—) | —(—) | —(—) | —(—) | P (P) | P (P) | P (P) |
| HM pectin (0.5%) | —(—) | —(—) | —(—) | —(—) | —(—) | —(—) | —(—) | —(—) |

"—", no change;
"P", precipitate formation;
"G", clear gel,
"G/P", cloudy gel;
Letter or sign in parentheses indicates the observations after keeping samples at 4° C. for 2 hr.

Cooling at 4° C. increases precipitate formation. Nevertheless, with 0.1% HMW *Aloe* pectin, a clear gel was formed at 0.15 and 0.2 M NaCl. This gel was reversible, changing back to a solution when brought back to room temperature. This reversible gelation could be performed over several times by changing between 4° C. and room temperature. Once changing back to the solution at room temperature, the preparation still gelled in-situ with the normal calf serum as described in Example 25.

These observations indicate that the precipitate or gel formation is related to low DM and HMW, i.e., the lower the DM and the higher the molecular weight, the more prone a pectin is to precipitation by a salt.

A marked difference was observed between NaCl and NH$_4$Cl; the concentration of NH$_4$Cl required for precipitate formation was much higher than that with NaCl. A similar pectin concentration-dependent effect was also observed. See Table 7. With the 0.5% HMW *Aloe* pectin, precipitate occurred at 0.6 M at room temperature and 0.4 M at 4° C.

The precipitates were whitish and could be fine or large granule-like depending on the salt concentration. The precipitates were the finest at the cut-off point or the salt concentration at which precipitates first appeared. This is in fact one efficient way to make pectin fine particles that can be used for drug delivery.

TABLE 7

|  | NH$_4$Cl (M) | | | | | | | |
| --- | --- | --- | --- | --- | --- | --- | --- | --- |
|  | 0 | 0.1 | 0.15 | 0.2 | 0.4 | 0.6 | 0.8 | 1.0 |
| HMW AP | | | | | | | | |
| 0.1% | —(—) | —(—) | —(—) | —(—) | —(—) | —(—) | —(P) | P (P) |
| 0.5% | —(—) | —(—) | —(—) | —(—) | —(G/P) | P (P) | P (P) | P (P) |
| LM pectin (0.5%) | —(—) | —(—) | —(—) | —(—) | —(—) | —(—) | —(—) | —(—) |
| HM pectin (0.5%) | —(—) | —(—) | —(—) | —(—) | —(—) | —(—) | —(—) | —(—) |

"—", no change;

"P", precipitate formation;

"G", clear gel,

"G/P", cloudy gel;

Letter or sign in parentheses indicates the observations after keeping samples at 4° C. for 2 hr.

Beyond revealing the fundamental properties of different pectins, these observations indicate that for preparing a liquid formulation with HMW *Aloe* pectin at a physiological ionic strength or as an isotonic solution (as embodied by 0.9% (w/v)-0.154 M NaCl) an alternative to NaCl is needed if the formulation needs to be stored as a solution at 4° C. and a pectin concentration >1 mg/ml will be used, as might be envisioned for a liquid in-situ gelling formulation physiological ionic strength of an unstable active agent such as a protein, which would need to be stored in a refrigerator. Precipitation of some or all of the pectin from such solution on cold storage would be highly undesirable. One such alternative salt that can be used in such a formulation is $NH_4Cl$, particularly at its concentration for an isotonic solution (0.84% (w/v) or 0.157 M, which is also equivalent to 0.154 M NaCl in ionic strength). At this concentration, $NH_4Cl$ also improves in-situ gelation of such liquid pectin-based pharmaceutical compositions.

EXAMPLE 26

In-situ Gelation of *Aloe* Pectin in the Nasal Cavity

An 0.5% *Aloe* pectin solution was prepared in 10 mM $NaH_2PO_4/Na_2HPO_4$ buffer, 0.84% $NH_4Cl$, pH 7.4, with or without a protein (BSA). The liquid formulation was delivered intranasally by dropping directly onto the nares of mice following anesthesia by inhalation of metofane, 20 µl/mouse evenly divided between the two nares. At 4 h post inoculation, mice were sacrificed and tissues were fixed in formalin. Serial cross sections were made of the nasal cavity starting anterior to the orbit of the eye.

Figure 10:
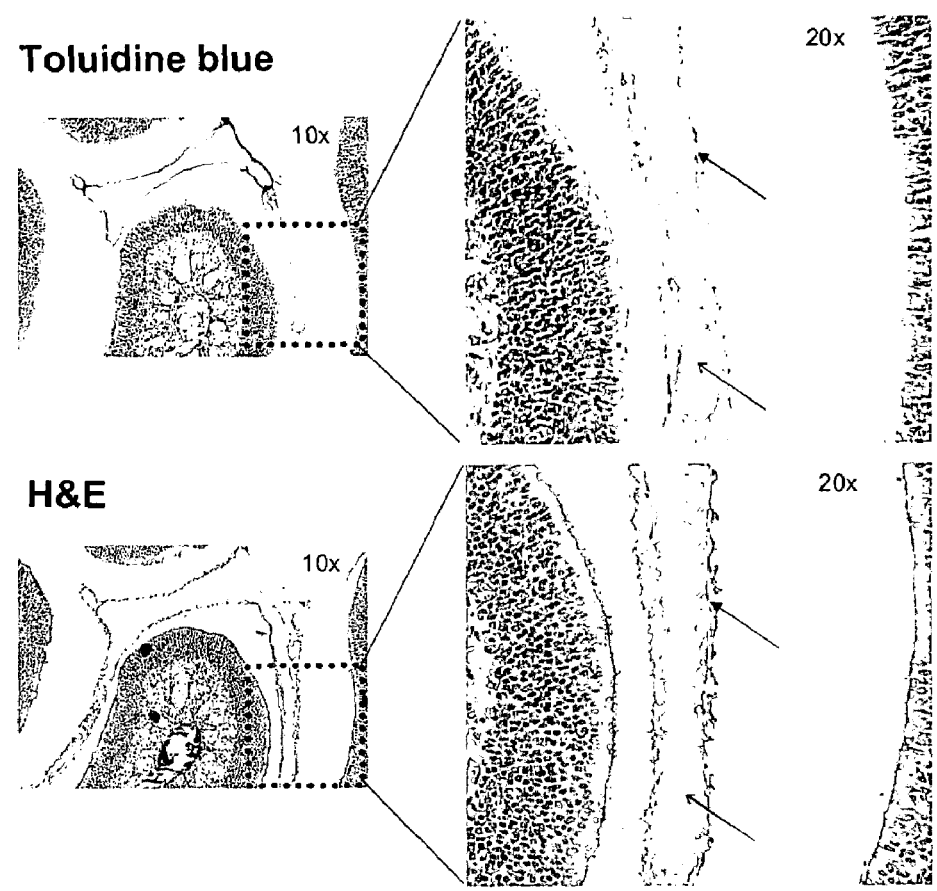
FIG. 10. Serial cross sections of the nasal cavity of a mouse 4 h after intranasal delivery of an HMW *Aloe* pectin solution (0.5%, w/v), showing formation of gel on the nasal mucosal surfaces, as described in Example 26.

The gel was detected by staining tissue sections with toluidine blue and H&E. The toluidine blue revealed in-situ gel as a pinkish/purplish substance, whereas the H&E stained the gel pale pinkish (FIG. 10). The gels were of various shapes and sizes, and could be found in various nasal cavity areas including those near the septum and middle and inferior concha.

To determine the effect of *Aloe* pectin concentration, *Aloe* pectin solutions at 0.25 or 0.5% were delivered intranasally to 2 mice per concentration. Gel formation was examined microscopically 4 hours after delivery. The area of gels in each section was measured by using ImageJ software (National Institute of Health) and expressed as $mm^2$. The gel areas on cross sections at the same position were used as an indirect measurement of the relative amounts of gel present in the nasal cavity. Thus, the results showed that more and larger gels were detected in the nasal cavity with 0.5% than 0.25%, suggesting that the amount of gel formed in the nasal cavity is polymer concentration-dependent.

EXAMPLE 27

Comparison with Other Pectins for In-situ Gelation in the Nasal Cavity

Various commercial LM pectins were used along with HMW *Aloe* pectins (Table 8). The commercial pectins, i.e., Genu pectins and polygalacturonic acid from Sigma Chemical Co., were used as purchased. One sample obtained by reprocessing Genu pectin LM12G was also used. It was dissolved in water, microfiltered, recovered by alcohol precipitation, and designated Genu pectin LM12G (R) after being dried under vacuum. The molecular weight of Genu pectin splendid type 100 was similar to other low molecular weight pectins (Table 8). Two different HMW *Aloe* pectin samples designated as A and B were used.

All commercial pectin samples were prepared as a 2% (w/v) solution in water and were then diluted 1:1 with a 2× saline solution (0.3 M NaCl). These commercial pectins produced a low pH when dissolved, i.e. 3-4. The pH of the solutions was adjusted to 6.5 with NaOH. The HMW *Aloe* pectins were prepared as above with a final concentration of 0.5% (w/v) in 0.84% (w/v) $NH_4Cl$. The pH of HMW *Aloe* pectin solution was 5.5-6.0 and no pH adjustment was made. All samples were delivered intranasally to mice as above, 2 mice per sample. Gel formation was examined 4 hrs later as above.

TABLE 8

| Pectins | DM | MW ($DA \times 10^5$) | Concentration (%, w/v) | Gel areas ($mm^2$) |
|---|---|---|---|---|
| Genu pectin LM12G | 31% | NA | 1 | 0.0075 |
| Genu pectin LM12G (R) | 31% | <2.0 | 1 | 0.0015 |
| Genu pectin LM18G | 40% | NA | 1 | none observed |
| Genu pectin splendid type 100 | 15% | 3.8 | 1 | none observed |
| Polygalacturonic acid, Sigma Chemical co | <3% | 1.7 | 1 | 0.0023 |
| HMW AP (A) | <10% | >10 | 0.5 | 0.049 |
| HMW AP (B) | <10% | >10 | 0.275 | 0.051 |

Two cross sections were made of the nasal cavity starting anterior to the orbit of the eye from each mouse. The gel area on the cross sections at the same position was used as an indirect measurement of the relative amounts of gel present in the nasal cavity. The total gel areas on all 4 sections from the two mice from each group was determined and divided by 4 to produce the average gel area per cross nasal section. The results showed that gels were detected with Genu pectin LM12G, Genu pectin LM12G (R), polygalacturonic acid, and HMW *Aloe* pectins, but no gel was detected with formulations employing the LM18G and Slendid Type 100 pectins, which are both pectins with low degrees of methylation and typical molecular weights. The areas of the gels detected with Genu LM12G and polygalacturonic acid were very limited or 6.5 to 33 fold smaller as compared to the gel areas measured for the formulation prepared from the HMW *Aloe* pectins, which were used at a concentration at least 2-fold lower concentrations (see Table 8). These results also illustrate the unexpectedly superior gellation properties of HMW *aloe* pectins, as compared to prior art pectins.

EXAMPLE 28

Nasal Residence Time of the In-situ Gel

To determine the nasal residence time of in-situ gel, an HMW *Aloe* pectin solution (5 mg/ml) in 0.84% (w/v) $NH_4Cl$ was delivered intranasally and gel formation was examined at various time points using two mice per time point. The relative amounts of gel present were determined by measuring the gel areas on nasal cavity tissue sections as above.

The results showed that gel was present in the nasal cavity through 24 h, but disappeared by 48 h (Table 9). Based on gel areas measured in the cross section of the nasal cavity, 50% clearance occurred at 24 h. Thus, the gel stayed in the nasal cavity between 24 and 48 h.

TABLE 9

| | Hours | | | | |
|---|---|---|---|---|---|
| | 1 | 4 | 8 | 24 | 48 |
| Presence of gel | Yes | Yes | Yes | Yes* | No |

*At 24 h post intranasal delivery, the amount of gel in the nasal cavity was reduced by >50% as measured by gel areas in the cross section of the nasal cavity.

EXAMPLE 29

Increased Immune Response Against DT-CRM and Influenza Antigens Following Intranasal Delivery with Liquid Formulations to Animals Antigens, animals and inoculation: Two antigens, DT-CRM (diphtheria toxin mutant CRM) and inactivated subvirion split influenza virus antigen (A/New Caledonia/20/99, H1N1), were used. Groups of 7 female 6-8 week old Balb/c mice were inoculated intranasally 2 or 3 times, 10 days apart with formulations consisting of antigen (0.5 mg/ml), HMW *Aloe* pectin (5 mg/ml for DT-CRM and 2.75 mg/ml for influenza), or a combination of both by dropping them directly onto the nostrils of mice (20 µl/mouse). The antigen dose was 10 µg/mouse. The antigen formulations were prepared in 0.84% $NH_4Cl$ and 10 mM phosphate buffer, pH 7.4

Sample collection and ELISA: Blood and lung wash samples were collected two weeks after the last inoculation. Specific serum IgG (immunoglobulin G) and lung IgA (immunoglobulin A) were measured by indirect ELISA (Enzyme-linked immunosorbent assay). For influenza (Flu), recombinant HA (Hemoagglutinin) protein of A/New Caledonia/20/99 (H1N1) obtained from Protein Science Co. was also used as an antigen for detecting HA-specific response. The end point for IgG titer was determined as the reciprocal of the highest dilution that has an absorbance value 50% greater than the background (absorbance of the antigen-coated wells without serum added). Each lung wash was assayed for antigen-specific and total IgA in two separate ELISA protocols. The results were expressed as ng (specific)/µg (total). To determine the level of antigen-specific IgA, the plates were coated with antigen and also serially diluted purified mouse IgA standard (1.0 to 0.002 µg/ml). The level of antigen-specific IgA was calculated from the standard curve generated with the absorbance values of the purified IgA standard. Total IgA was determined by a sandwich ELISA with purified mouse IgA as a standard.

Mean IgG titers in serum and specific to total IgA ratios in lung wash along with their standard errors were determined for every group of mice. Means were compared using Student's t test. A serum sample having a titer >10 or a lung wash sample having a specific/total IgA ratio 2 times higher than the control was considered a responder.

Results

Strong serum IgG and lung IgA responses were only obtained when antigens were delivered with *Aloe* pectin. Minimal or no response was detected with antigen alone.

DT-CRM: The serum IgG and lung IgA responses were significantly higher when antigen was combined with *Aloe* pectin than antigen given alone after either single or multiple inoculations. The peak response was detected at week 3 with *Aloe* pectin/DT-CRM after single inoculation. The response was also initiated faster with *Aloe* pectin/DT-CRM, detectable at week 2.

Figure 11:
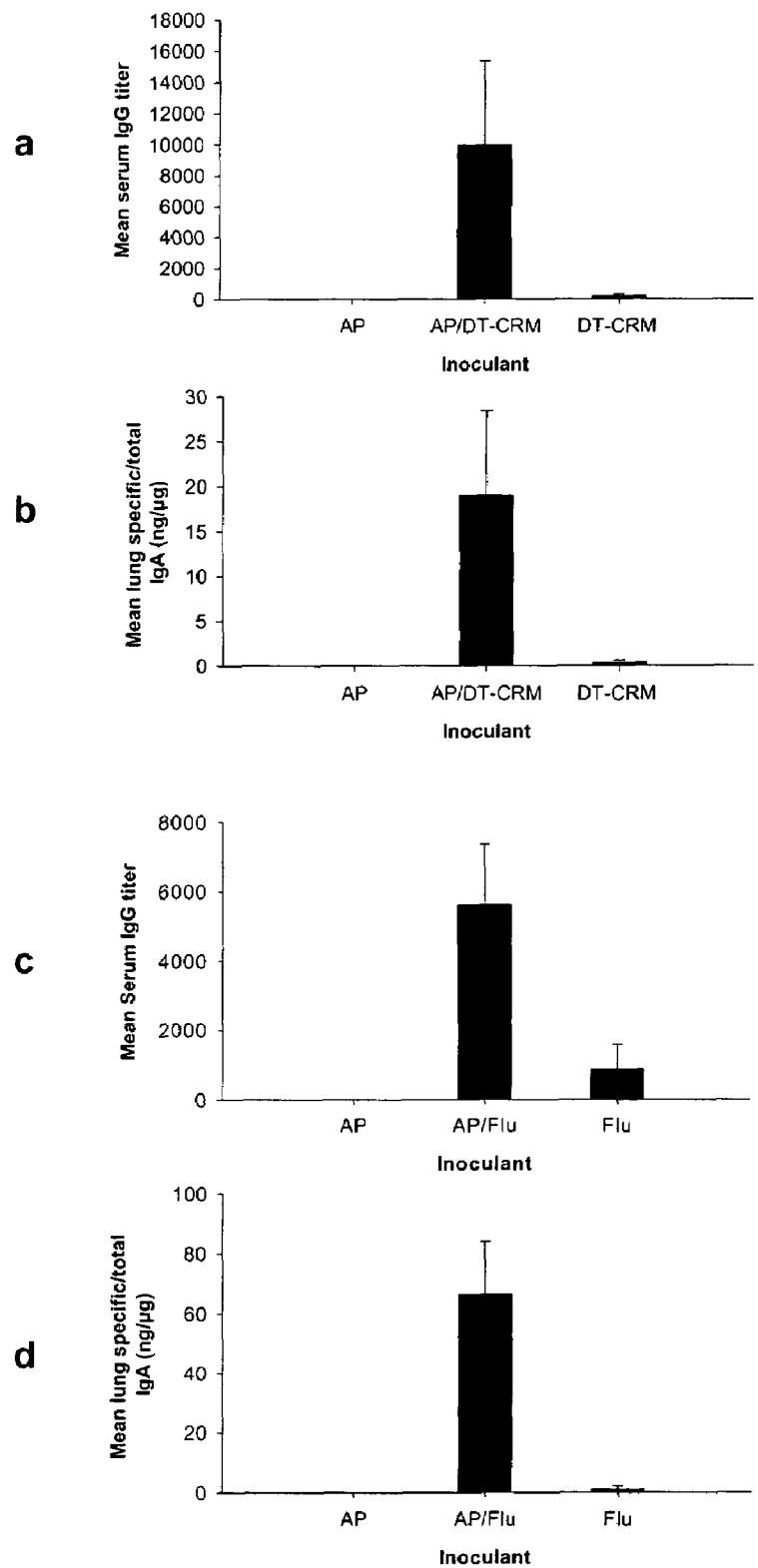
FIG. 11. Serum IgG and lung IgA immunological responses of mice to nasal administration of liquid vaccine compositions comprising *aloe* pectin and a protein antigen (DT-CRM) (a and b) or an inactivated influenza split sub-virion antigen (A/New Caledonia/20/99, H1N1) (c and d), as described in Example 29.

After three inoculations, mice in the *Aloe* pectin/DT-CRM group had serum IgG and lung IgA titers that were significantly higher (50 or 100 times, respectively) than the DT-CRM alone group (FIGS. 11a and 11b). In addition, all 7 mice in the *Aloe* pectin/DT-CRM group responded with both serum IgG and lung IgA, whereas only 4 of 7 responded with serum IgG and 3 of 7 with lung IgA in the group given DT-CRM alone. No response was detected in the *Aloe* pectin alone group.

Influenza: After two inoculations, mice receiving *Aloe* pectin/Flu antigen had significantly higher serum IgG (6 times) and lung IgA (60 times) titers than the group given the Flu antigen alone (FIGS. 11c and 11d). For serum IgG, all 7 mice in both *Aloe* pectin/Flu antigen and Flu antigen alone groups responded. However, for lung IgA, 6 of 7 responded in the *Aloe* pectin/Flu antigen group and only 1/7 in the Flu antigen alone group. No response was detected in the *Aloe* pectin alone group.

The same results were also obtained when recombinant HA protein was used as the antigen in ELISA for measuring HA-specific IgG or IgA.

EXAMPLE 30

Use of pH to Control Gelation or Precipitate Formation of Powder Formulations

There are many polymers that gel or form precipitate in response to a change in pH. For example, chitosan glutamate is soluble at a pH up to 6.5. But beyond pH 6.5, it becomes insoluble, forming precipitates or gel-like substance which can be used for controlled drug delivery. Thus, a liquid drug formulation with chitosan is prepared at pH 6.5 or lower and made into a dry powder using a method described above. Following delivery, these particles can be partially or completely dissolved due to its internal buffering capacity, although they may be hydrated by a bodily fluid or secretion having a pH of 7.0-7.4. In the case of intranasal delivery, however, the nasal fluids are acidic and can have a pH as low as 5.5 (England et al., Clinical Otolaryggology 24, 67-68, 1999; Ireson et al., Clinical Science 100, 327-333, 2001).

Thus, the formulation powder is then blended with an appropriate amount of buffer powder such as a phosphate buffer at pH 7.4. Upon delivery and hydration, the buffer agents will be quickly dissolved upon hydration, ensuring the local environment at pH 7.4 and thereby keeping the formulation particles insoluble or insoluble for a longer period of time.

Throughout this application, various publications and patents are referenced. The disclosures of these publications and patents are hereby incorporated by reference into this application in their entirety, for all purposes, especially for their teachings regarding formulation of pharmaceutical compositions.

While the preferred compositions or formulations and methods have been disclosed, it will be apparent to those skilled in the art that numerous modifications and variations are possible in light of the above teaching. It should also be realized by those skilled in the art that such modifications and variations do not depart from the spirit and scope of the invention as set forth in the appended claims.

What is claimed is:

1. A solid pharmaceutical composition for the delivery of a physiologically active agent to an animal comprising:

a. one or more physiologically active agents selected from the group consisting of peptides, proteins, vaccines comprising one or more antigens, dead cells in whole or in part, and viruses in whole or in part, in an amount effective to induce a physiological response in the animal;

b. one or more *Aloe* pectins having a degree of methylation less than about 50% and in an amount of about 0.25% to about 2%, based on the total weight of the solid pharmaceutical composition; and c. one or more solid, pharmaceutically acceptable salts of a divalent or multivalent metal cation;

wherein the pharmaceutical composition is in a powder form that forms a gel when contacted with a tissue or body fluid of an animal, and wherein the powder comprises a plurality of microparticles and/or microspheres having a particle size that permits the microparticles or microspheres to pass through a sieve having an opening size of about 250 µM in diameter.

2. The solid pharmaceutical composition of claim 1, further comprising alginate, carrageenan, or gellan.

3. The solid pharmaceutical composition of claim 1 wherein the one or more *Aloe* pectins have a degree of methylation of less than 25%.

4. The solid pharmaceutical composition of claim 1 wherein the one or more *Aloe* pectins have a degree of methylation of less than 10%.

5. The solid pharmaceutical composition of claim 1 wherein the one or more *Aloe* pectins have an average molecular weight of greater than about $4.0 \times 10^5$ Daltons.

6. The solid pharmaceutical composition of claim 1 wherein the one or more *Aloe* pectins have an average molecular weight of greater than about $1.0 \times 10^6$ Daltons.

7. The solid pharmaceutical composition of claim 1 wherein the one or more *Aloe* pectins have an average molecular weight of greater than about $1.0 \times 10^6$ Daltons, and a degree of methylation of less than about 10%.

8. The solid pharmaceutical composition of claim 1 wherein the one or more *Aloe* pectins have a galacturonic acid content of greater than about 80% w/w.

9. The solid pharmaceutical composition of claim 1 wherein the one or more *Aloe* pectins have a rhamnose content of greater than 4% by mole.

10. The solid pharmaceutical composition of claim 1 wherein the tissue or body fluid is normal calf serum.

11. The solid pharmaceutical composition of claim 1 wherein the one or more physiologically active agents comprise a peptide or a protein.

12. The solid pharmaceutical composition of claim 1 wherein the one or more physiologically active agents comprises a vaccine.

13. The solid pharmaceutical composition of claim 12 wherein the vaccine comprises one or more antigens.

14. The solid pharmaceutical composition of claim 1 wherein the divalent or multivalent metal cation is magnesium, copper, manganese, nickel, cobalt, iron, or zinc.

15. The solid pharmaceutical composition of claim 1 wherein the divalent or multivalent metal cation is calcium or aluminum.

16. The solid pharmaceutical composition of claim 1 wherein the one or more pharmaceutically acceptable salt is soluble in water to the extent of at least about $1 \times 10^{-5}$ moles per liter.

17. The solid pharmaceutical composition of claim 1 wherein the one or more pharmaceutically acceptable salt will not dissolve in water to form a solution comprising at least $1 \times 10^{-5}$ moles per liter.

18. The solid pharmaceutical composition of claim 1 wherein the one or more pharmaceutically acceptable salts comprise aluminum hydroxide or calcium phosphate.

19. The solid pharmaceutical composition of claim 1 further comprising one or more pharmaceutically acceptable excipients.

20. The solid pharmaceutical composition of claim 19 wherein the one or more pharmaceutically acceptable excipients are selected from the group consisting of binders, fillers or bulking agents, lubricants, flavors, and taste masking agents.

21. The solid pharmaceutical composition of claim 1 further comprising one or more pharmaceutically acceptable thickeners.

22. The solid pharmaceutical composition of claim 21 wherein the one or more pharmaceutically acceptable thickeners are selected from the group consisting of carboxymethylcellulose, hydroxypropylmethylcellulose, collagen, gelatin, dextran, and hyaluronic acid.

23. The solid pharmaceutical composition of claim 21 wherein the one or more pharmaceutically acceptable thickeners comprise polyvinylpyrrolidone.

24. The solid pharmaceutical composition of claim 1 wherein the animal is a human.

25. A method for the sustained release of a physiologically active agent to an animal comprising administering the solid pharmaceutical composition of claim 1 to a tissue or body fluid of an animal, to form a gel in contact with the tissue or body fluids of the animal.

26. A method for the sustained release of a physiologically active agent to an animal comprising administering a liquid suspension of the solid pharmaceutical composition of claim 1, or the components thereof, to a tissue or body fluid of an animal to form a gel in contact with the tissue or body fluids of the animal.

27. The method of claim 26 wherein the tissues or body fluid of the animal are selected from the group consisting of mucosal surfaces, blood, serum, tear fluid, lung fluid, interstitial fluid, or nasal secretions.

28. The method of claim 26 wherein the animal is a human.

29. The method of claim 26 wherein the tissues or body fluids of the animal are nasal mucosal surfaces or nasal secretions.

30. A composition for the controlled release of a physiologically active agent to an animal comprising:

a. one or more physiologically active agents selected from peptides, proteins, vaccines comprising one or more antigens, dead cells in whole or in part, or viruses in whole or in part, in an amount effective to induce a physiological response in the animal; and b. one or more pectic substances having a degree of methylation less than about 30% and an average molecular weight of greater than about $1 \times 10^{-5}$ Daltons in an amount of about 0.25% to about 2%, based on the total weight of the composition, wherein the composition is a powder that forms a gel when contacted with a tissue or body fluid of an animal, and wherein the powder comprises microparticles and/or microspheres that have an particle size that permits the microparticles or microspheres to pass through a sieve having an opening size of about 250 µM in diameter.

31. The composition of claim 30 wherein the pectic substance has a degree of methylation less than about 15%.

32. The composition of claim 30 wherein the pectic substance has an average molecular weight of greater than about $5.0 \times 10^5$ Daltons.

33. The composition of claim 30 wherein the pectic substance has a molecular weight greater than $1 \times 10^6$ Daltons and a degree of methylation of less than 10%.

34. The composition of claim 30 wherein the pectic substance has a galacturonic acid content of greater than about 90% w/w.

35. The composition of claim 30 wherein the pectic substance comprises 3-methoxy-rhamnose.

36. The composition of claim 30 wherein the pectic substance has a rhamnose content of greater than 4% by mole.

37. The composition of claim 30 wherein the pectic substance is an *Aloe* pectin.

38. The composition of claim 30 wherein the composition comprises about 20% water by weight, or less.

39. The composition of claim 30 wherein the powder comprises at least about 80% by weight of microparticles and/or microspheres having particle sizes that permits the microparticles and/or microspheres to pass through a sieve having an opening size of 100 µM in diameter but not pass through a sieve having an opening size of about 0.1 µM in diameter.

40. The composition of claim 30 consisting essentially of microparticles and/or microspheres, wherein the microparticles and/or microspheres having particle sizes that permits them to pass through a sieve having an opening size of about 50 µM in diameter but not pass through a sieve having an opening size of 10 µM in diameter.

41. The composition of claim 30 wherein the solid composition comprises microspheres, wherein less than 90% of the microspheres have a diameter between 0.1 and 10 µM.

42. The composition of claim 30 further comprising one or more pharmaceutically acceptable thickeners.

43. The composition of claim 42 wherein the one or more thickeners are selected from the group consisting of carboxymethylcellulose, hydroxypropylmethylcellulose, collagen, gelatin, dextran, hyaluronic acid, or alginate.

44. The composition of claim 42 wherein the one or more thickeners comprise polyvinylpyrrolidone.

45. The composition of claim 42 wherein the thickener comprises from about 0.1 to about 90% of the composition by weight.

46. The composition of claim 30 wherein the one or more physiologically active agents comprise a peptide or a protein.

47. The composition of claim 30 wherein the one or more physiologically active agents comprises a vaccine.

48. The composition of claim 47 wherein the vaccine comprises one or more antigens.

49. The composition of claim 48 wherein the vaccine induces an active immune response in the animal when the composition is administered to the nasal mucosa of the animal.

50. The composition of claim 30 further comprising a solid polysaccharide gel inducing agent.

51. The composition of claim 50 wherein the solid polysaccharide gel inducing agent comprises one or more pharmaceutically acceptable salts of a divalent or multivalent metal cation.

52. The composition of claim 51 wherein the divalent or multivalent metal cation is calcium, magnesium, copper, manganese, nickel, cobalt, iron, zinc, or aluminum.

53. The composition of claim 51 wherein the pharmaceutically acceptable salt can dissolve in water to form a solution comprising at least about $1 \times 10^{-5}$ moles per liter of the salt.

54. The composition of claim 51 wherein the pharmaceutically acceptable salt is a calcium salt.

55. The composition of claim 51 wherein the pharmaceutically acceptable salt is a calcium halide salt.

56. The composition of claim 51 wherein the pharmaceutically acceptable salt is sufficiently insoluble in water so as to not be capable of dissolving in water to form a solution comprising at least $1 \times 10^{-5}$ moles per liter of the salt.

57. The composition of claim 51 wherein the one or more pharmaceutically acceptable salts comprise aluminum hydroxide or calcium phosphate.

58. The composition of claim 51 wherein the one or more pharmaceutically acceptable salts comprise from about 0.1% to about 80% (w/w) of the composition.

59. The composition of claim 51 wherein the one or more divalent or multivalent metal cation salts react with the pectic substance to crosslink the carboxylate groups of the pectic substance so as to form a gel comprising the metal cation.

60. The composition of claim 51 wherein the one or more divalent or multivalent metal cation salts induce the composition to form a gel when the composition is contacted with the tissue or body fluid of an animal.

61. The composition of claim 30 wherein the tissues or body fluids of the animal are selected from the group consisting of mucosal surfaces, blood, serum, tear fluid, lung fluid, or interstitial fluid.

62. The composition of claim 30 wherein the tissues or body fluids of the animal are nasal secretions.

63. A method for the sustained release of a physiologically active agent to an animal comprising contacting the composition of claim 30 with a tissue or body fluid of the animal.

64. The method of claim 63 wherein the composition forms a gel comprising the physiologically active agent in contact with the tissues or body fluids on or after administration to the tissues or body fluids.

65. The method of claim 63 wherein the gel provides a sustained time release of the physiologically active agent to the tissues or body fluids.

66. The gel formed by the process of claim 65.

67. A method for the sustained release of a physiologically active agent to an animal comprising administering a liquid suspension of the solid pharmaceutical composition of claim 30, or the components thereof, to a tissue or body fluid of an animal to form a gel in contact with the tissue or body fluids of the animal.

68. A method for the sustained release of a physiologically active agent to an animal comprising contacting the composition of claim 30 with an eye, a mucosal surface, or a wound of the animal.

69. A method for the sustained release of a physiologically active agent to an animal comprising contacting the composition of claim 30 with one or more bodily fluids of the animal selected from the group consisting of blood, serum, tear fluid, lung fluids, interstitial fluid, or nasal secretions.

70. A method for the sustained release of a physiologically active agent to an animal comprising administering the composition of claim 30 to the nasal mucosal surfaces and secretions of a human.

71. A method of making the composition of claim 30 comprising mixing in any sequence the physiologically active agent, the pectic substance, and one or more optional components and processing the mixture to form the solid composition.

72. The method of claim 71 wherein the one or more optional components comprise a thickener.

73. The method of claim 71 wherein the one or more optional components comprise a polyvinyl pyrrolidone.

74. The method of claim 71 wherein the physiologically active agent and the pectic substance are dissolved in a liquid carrier, then the volatile components of the liquid carrier are removed to form the solid composition.

75. The method of claim 71 wherein the physiologically active agent, the pectic substance, and any optional components are solids and are mixed and processed as solids.

76. The method of claim 71 wherein the optional component comprises a solid gel inducing agent comprising one or more pharmaceutically acceptable salts of a divalent or multivalent metal cation.

77. A method for administering a vaccine to an animal, comprising administering to the animal's mucosal surfaces:

a. one or more powders comprising microspheres or microparticles that have an particle size that permits the microparticles or microspheres to pass through a sieve having an opening size of about 250 μM in diameter, and that separately or together comprise i) a pectic substance having a degree of methylation less than about 30% and an average molecular weight of greater than $1\times10^5$ Daltons, in an amount of about 0.25% to about 2% based on the total weight of the composition;

ii) one or more antigens selected from the group consisting of a peptide, a protein, a nucleic acid, a dead cell or a portion thereof, and a virus, in an amount that is capable of inducing an active immune response in the animal.

78. The solid pharmaceutical composition of claim 1 wherein the one or more *Aloe* pectins have an average molecular weight of greater than about $1.0\times10^5$ Daltons.

* * * * *